(12) United States Patent
Yoshimura et al.

(10) Patent No.: US 7,241,860 B1
(45) Date of Patent: Jul. 10, 2007

(54) TRANSCRIPTION FACTOR POLYPEPTIDE THAT REGULATES CHONDROMODULIN-I EXPRESSION

(75) Inventors: Koji Yoshimura, Ibaraki (JP); Yuichi Hikichi, Ibaraki (JP); Kenichi Noguchi, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 428 days.

(21) Appl. No.: 10/130,872

(22) PCT Filed: Nov. 24, 2000

(86) PCT No.: PCT/JP00/08257

§ 371 (c)(1),
(2), (4) Date: May 22, 2002

(87) PCT Pub. No.: WO01/38392

PCT Pub. Date: May 31, 2001

(51) Int. Cl.
*A61K 38/17* (2006.01)
*C12P 21/02* (2006.01)
*C12Q 1/68* (2006.01)

(52) U.S. Cl. ............... 530/300; 530/350; 435/70.1; 435/7.1

(58) Field of Classification Search ............... None
See application file for complete search history.

(56) References Cited

U.S. PATENT DOCUMENTS 5,851,775 A * 12/1998 Barker et al. ............... 435/6

FOREIGN PATENT DOCUMENTS

EP 0 473 080 A2 3/1992
JP 07-138295 5/1995

OTHER PUBLICATIONS

Y. Hiraki, et al.; "Identification of Chondromodulin I as a Novel Endothelial Cell Growth Inhibitor"; J. of Biological Chemistry; vol. 272; No. 51; pp. 32419-32426; 1997.

Y. Hiraki, et al.; "Molecular Cloning of a New Class of Cartilage-Specific Matrix, Chondromodulin-I, Which Stimulates Growth of Cultured Chondrocytes"; Biochemical and Biophysical Research Communications; vol. 175; No. 3; pp. 971-977; 1991.

Yanagihara, et al., "Genomic Organization of the Human Chondromodulin-I Gene Containing a Promoter Region That Confers the Expression of Reporter Gene in Chondrogenic ATDC5 Cells," Journal of Bone and Mineral Research, vol. 15, No. 3, Mar. 2000, pp. 421-429.

Shukunami, et al., "Generation of Multiple Transcripts from the Chicken Chondromodulin-I Gene and Their Expression During Embryonic Development," FEBS Letters. Netherlands Jul. 30, 1999, vol. 456, No. 1, pp. 165-170.

* cited by examiner

*Primary Examiner*—Celine Qian
*Assistant Examiner*—Jennifer Dunston
(74) *Attorney, Agent, or Firm*—David G. Conlin; Christine C. O'Day; Edwards Angell Palmer & Dodge LLP

(57) ABSTRACT

The polypeptide of the present invention has an activity of binding specifically to the cis-element of Chondromodulin-I (ChM-I) gene promoter and promoting the transcription of the ChM-I gene. The polypeptide of the present invention is usable in screening for a compound that promotes or inhibits the activity of the polypeptide.

7 Claims, 5 Drawing Sheets

FIG. 1

```
AGGTGAGGCGGCTGGAAGGGTGGGACCCCTGGCTGGCC  human
AGGTGAGGCGGCTAGAAGGGTGGGGACCCGCTGGCTGGCC  hunChm-I_suzuki CAGGGCGGGACCGTGCACCCGGTGTGGCCCGTTGAAAC  human
CAGGGCGGGACCGTGCACCCGGTGTGGCCCGTTGAAAC  hunChm-I_suzuki TGCCTGGCTTCGGCACCGGGAGGACAGATCCCCAGGTGC  human
TGCCTGCCGTCGGCACCGGGAGGACAGATCCCCAGGTGC  hunChm-I_suzuki CCAGGGAGTCTCCAAAGTGCCCTCACTCCCTCCGCAAAC  human
CCAGGGAGTCTCCAAAGTGCCCTCACTCCCTCCGCAAAC  hunChm-I_suzuki ATG  human
ATG  hunChm-I_suzuki
```

FIG.3

```
         10        20        30        40        50        60        70        80        90       100
GACCAGAAGCTGCAGGTCTGCTGCAGGGTGGAGGAGGTGTGGCTGGCAAAACTGCAGGGCCCCTGTCCCCAGGCACCACCCCTGGAGCCCGGAGCCCAGG
  D  Q  K  L  Q  V  C  C  R  V  E  E  V  W  L  A  K  L  Q  G  P  C  P  Q  A  P  P  L  E  P  G  A  Q  A 110       120       130       140       150       160       170       180       190       200
CCCTGGCCTACAGGCCCGTCTCCAGGAACATCGATGTCCCAAAGAGGAAGTCGGACGCAGTGGAAATGGATGAGATGATGGCGGCCATGGTGCTGACGTC
  L  A  Y  R  P  V  S  R  N  I  D  V  P  K  R  K  S  D  A  V  E  M  D  E  M  M  A  A  M  V  L  T  S 210       220       230       240       250       260       270       280       290       300
CCTGTCCTGCAGCCCTGTTGTACAGAGTCCTCCCGGGACCGAGGCCAACTTCTCTGCTTCCCGTGCGGCCTGCGACCCATGGAAGGAGAGTGGTGACATC
  L  S  C  S  P  V  V  Q  S  P  P  G  T  E  A  N  F  S  A  S  R  A  A  C  D  P  W  K  E  S  G  D  I 310       320       330       340       350       360       370       380       390       400
TCGGACAGCGGCAGCAGCACTACCAGCGGTCACTGGAGTGGGAGCAGTGGTGTCTCCACCCCCTCGCCCCCCCACCCCCAGGCCAGCCCCAAGTATTTGG
  S  D  S  G  S  S  T  T  S  G  H  W  S  G  S  S  G  V  S  T  P  S  P  P  H  P  Q  A  S  P  K  Y  L  G 410       420       430       440       450       460       470       480       490       500
GGGATGCTTTTGGTTCTCCCCAAACTGATCATGGCTTTGAGACCGATCCTGACCCTTTCCTGCTGGACGAACCAGCTCCACGAAAAAGAAAGAACTCTGT
  D  A  F  G  S  P  Q  T  D  H  G  F  E  T  D  P  D  P  F  L  L  D  E  P  A  P  R  K  R  K  N  S  V 510       520       530       540       550       560       570       580       590       600
GAAGGTGATGTACAAGTGCCTGTGGCCAAACTGTGGCAAAGTTCTGCGCTCCATTGTGGGCATCAAACGACACGTCAAAGCCCTCCATCTGGGGGACACA
  K  V  M  Y  K  C  L  W  P  N  C  G  K  V  L  R  S  I  V  G  I  K  R  H  V  K  A  L  H  L  G  D  T 610       620       630       640       650       660       670       680       690       700
GTGGACTCTGATCAGTTCAAGCGGGAGGAGGATTTCTACTACACAGAGGTGCAGCTGAAGGAGGAATCTGCTGCTGCTGCTGCTGCTGCCGCAGGCA
  V  D  S  D  Q  F  K  R  E  E  D  F  Y  Y  T  E  V  Q  L  K  E  E  S  A  A  A  A  A  A  A  A  G  T 710       720       730       740       750       760       770       780       790       800
CCCCAGTCCCTGGGACTCCCACCTCCGAGCCAGCTCCCACCCCCAGCATGACTGGCCTGCCTCTGTCTGCTCTTCCACCACCTCTGCACAAAGCCCAGTC
  P  V  P  G  T  P  T  S  E  P  A  P  T  P  S  H  T  G  L  P  L  S  A  L  P  P  P  L  H  K  A  Q  S 810       820       830       840       850       860       870       880       890       900
CTCCGGCCCAGAACATCCTGGCCCCGGAGTCCTCCCTGCCCTCAGGGGCTCTCAGCAAGTCAGCTCCTGGGTCCTTCTGGCACATTCAGGCAGATCATGCA
  S  G  P  E  H  P  G  P  E  S  S  L  P  S  G  A  L  S  K  S  A  P  G  S  F  W  H  I  Q  A  D  H  A 910       920       930       940       950       960       970       980       990      1000
TACCAGGCTCTGCCATCCTTCCAGATCCCAGTCTCACCACACATCTACACCAGTGTCAGCTGGGCTGCTGCCCCCCTCCCCCGCCTGCTCTCTCTCTCCGG
  Y  Q  A  L  P  S  F  Q  I  P  V  S  P  H  I  Y  T  S  V  S  W  A  A  A  P  S  A  A  C  S  L  S  P  V 1010      1020      1030      1040      1050      1060      1070      1080      1090      1100
TCCGGAGCCCGGTCGCTAAGCTTCAGCCAGCCCCAGCAGCCAGCACCTGCGATGAAATCTCATCTGATCGTCACTTCTCCACCCCCGGCCCAGAGTGGTGC
  R  S  R  S  L  S  F  S  E  P  Q  Q  P  A  P  A  M  K  S  H  L  I  V  T  S  P  P  R  A  Q  S  G  A 1110      1120      1130      1140      1150      1160      1170      1180      1190      1200
CAGGAAAGCCCGAGGGGAGGCTAAGAAGTGCCGCAAGGTGTATGGCATCGAGCACCGGGACCAGTGGTGCACGGCCTGCCGGTGGAAGAAGGCCTGCCAG
  R  K  A  R  G  E  A  K  K  C  R  K  V  Y  G  I  E  H  R  D  Q  W  C  T  A  C  R  W  K  K  A  C  Q 1210      1220      1230      1240      1250      1260      1270      1280      1290      1300
CGCTTTCTGGACTGAGCTGTGCTGCAGGTTCTACTCTGTTCCTGGCCCTGCCGGCAGCCACTGACAAGAGGCCAGTGTGTCACCAGCCCTCAGCAGAAAC
  R  F  L  D  -

1310      1320      1330      1340      1350      1360      1370      1380      1390      1400
CGAAACAGAAAGAACGGAAACACGGAGTTTGGGCTCTGTTGGCTAAGGTGTAACACTTAAAGCAATTTTCTCCCATTGTGCGAACATTTTATTTTTTAAA 1410      1420      1430      1440      1450      1460      1470      1480      1490      1500
AAAAAGAAACAAAAATATTTTTCCCCCTAAAATAGGAGAGAGCCAAAACTGACCAAGGCTATTCAGCAGTGAACCAGTGACCAAAGAATTAATTACCCTC 1510      1520      1530      1540      1550      1560      1570      1580      1590      1600
CGTTTCCCACATCCCCACTCTCTAGGGGATTAGCTTGTGCGTGTCAAAAGAAGGAACAGCTCGTTCTGCTTCCTGCTGAGTCGGTGAATTCTTTGCTTTC 1610      1620      1630      1640      1650      1660      1670
TAAACTCTTCCAGAAAGGACTGTGAGCAAGATGAATTTACTTTTCTTAAAAAAAAAAAAAAAAAAAAA
```

FIG. 4

```
        10        20        30        40        50        60        70        80        90       100
TGGGTCTTTGGGGAGGCAGGTTCCCAAGTGAGTTTATTTACCTTGAGTTGATCGATATTTGTTACATGTCCTCCTAGGAACAGGGATTATTATTTCTGTA 110       120       130       140       150       160       170       180       190       200
AAAAGAAAAGATAGAGCAGGCCATGGCGGCCCAACAGGTAAAGCAGCTCGCCACCAAACCACCAAACCTGATGTCCTGACTTTGATCCTTGCTGTCTACA 210       220       230       240       250       260       270       280       290       300
TGGTGAAAGAGAGAGCTGAGTCCTGCCAGGCTCTTCTCTGACTGTCACGAATGTGCCATGGCATACACACACAGAAAAGAGAGAGAGAGAGAGAGAGACAG 310       320       330       340       350       360       370       380       390       400
ACAGACAGACACTGACTGACTGACTGCCCTTTTTGTCTCAGCAGGCGGAGCAGAGTATCCAGCATGCTGTCCCGACGCCTTGGTAAGCGCTCCCTCTTGG
                                                            M  L  S  R  R  L  G  K  R  S  L  L  G 410       420       430       440       450       460       470       480       490       500
GAGCCCGGGTGTTGGGACCTAGTGCCGCTGAAGTACCATCAGGGGCCACCCTGCCTCTGGAGCCACAGATAGAAGTGCCGGAAGGAGCCATGTCCCTGTC
  A  R  V  L  G  P  S  A  A  E  V  P  S  G  A  T  L  P  L  E  P  Q  I  E  V  P  E  G  A  M  S  L  S 510       520       530       540       550       560       570       580       590       600
CCCACTCACCTCTAAGGACCCTGTGTGCCAGGAGCAGCCCAAGGAGCTCCTCAAAGCTCTGGGAACCTCAGGCCACCCACAGGTGGCCTTTCAGCCTGCA
  P  L  T  S  K  D  P  V  C  Q  E  Q  P  K  E  L  L  K  A  L  G  T  S  G  H  P  Q  V  A  F  Q  P  G 610       620       630       640       650       660       670       680       690       700
CAGAAGGTCTGTGTGTGGTATGGAGGTCAGGAGTGCAAGGGCCTGGTGGAGCAGCACAGCTGGGCCGAGGACAAGGTGACCGTCCGGCTGCTGGACCAGA
  Q  K  V  C  V  W  Y  G  G  Q  E  C  K  G  L  V  E  Q  H  S  W  A  E  Q  K  V  T  V  R  L  L  D  Q 710       720       730       740       750       760       770       780       790       800
AGTTACAGATTCGCTGTAAAGTGGAAGAGGTGTGGCTGGCGGAGCTGCAGGGTAGCGCATCCCACGTGCCAGCCTTGCAGCCCCGCAGCCCAGGTGCCAGC
  K  L  Q  I  R  C  K  V  E  E  V  W  L  A  E  L  Q  G  S  A  S  H  V  P  A  L  E  P  G  A  Q  V  P  A 810       820       830       840       850       860       870       880       890       900
CTACAGACCCGTGTCTAGGAACATCGACGTCCCGAAGAGGAAGTCGGATGCGGTGGAGATGGACGAGATGATGGCCGCCATGGTGCTGACGTCTCTGTCT
  Y  R  P  V  S  R  N  I  D  V  P  K  R  K  S  D  A  V  E  M  D  E  M  M  A  A  M  V  L  T  S  L  S 910       920       930       940       950       960       970       980       990      1000
TGCAGTCCCGTTGTGCAGAGTCCTCCTGGGGCTGAGCCCATCTTCTCTGTTTCCGTGCAGCCTGCGGTGACCCGTGGAAGGAGAGCGGTGATGTTTCAG
  C  S  P  V  V  Q  S  P  P  G  A  E  P  I  F  S  V  S  R  A  A  C  G  D  P  W  K  E  S  G  D  V  S  D 1010      1020      1030      1040      1050      1060      1070      1080      1090      1100
ACAGCGGCAGCAGCCGGCACTGAGCGGGAGCAGTGGCAGCTCTACCCCTCGCCGCCCCATCCGCAGGCCAGCCCCAAGTACCTGGGGGATGCCTTTGG
  S  G  S  S  G  H  W  S  G  S  S  G  S  S  T  P  S  P  P  H  P  Q  A  S  P  K  Y  L  G  D  A  F  G 1110      1120      1130      1140      1150      1160      1170      1180      1190      1200
GTCTCCCCAAACTGATCATGGCTTTGAGACTGATCCTGACCCTTTCCTGTTAGACGAACCAGCCCCACGAAAGAGGAGGAACTCCGTGAAGGTGATGTAC
  S  P  Q  T  D  H  G  F  E  T  D  P  D  P  F  L  L  D  E  P  A  P  R  K  R  R  N  S  V  K  V  M  Y 1210      1220      1230      1240      1250      1260      1270      1280      1290      1300
AAGTGCCTGTGGCCCAGCTGTGGCAAAGTTCTCCGTTCAATTGTGGGCATCAAACGACACGTCAAAGCCCTCCACCTGGGGGACACTGTTGACTCTGATC
  K  C  L  W  P  S  C  G  K  V  L  R  S  I  V  G  I  K  R  H  V  K  A  L  H  L  G  D  T  V  D  S  D  Q 1310      1320      1330      1340      1350      1360      1370      1380      1390      1400
AGTTCAAGCGGGAGGAAGACTTTTACTACACAGAGATGCAGATGAAAGAGGAATCTGCTCAGGCTGTGGCTGCTCCCCCTGCCCCTGGGACACCTATGGG
  F  K  R  E  E  D  F  Y  Y  T  E  M  Q  M  K  E  E  S  A  Q  A  V  A  A  P  P  A  P  G  T  P  M  G 1410      1420      1430      1440      1450      1460      1470      1480      1490      1500
CGAGCCAGCGTCCACCTCCAGGGTGACCAGCCCGTCCCTTGCTGCTCTTTCATTGCCTCCAGCCAAGGTCCAGTCATCTGGCCCAGAACACCCTGGCCTG
  E  P  A  S  T  S  R  V  T  S  P  S  L  A  A  L  S  L  P  P  A  K  V  Q  S  S  G  P  E  H  P  G  L 1510      1520      1530      1540      1550      1560      1570      1580      1590      1600
GAGTCTTCTCTGCCCTCAGTTGCACTCAGCAAGTCAGCTCCTGGCTCTTCTGGCACATTCAGGCTGACCATGCATATCAGGCTCTGCCATCCTTCCAGA
  E  S  S  L  P  S  V  A  L  S  K  S  A  P  G  S  F  W  H  I  Q  A  D  H  A  Y  Q  A  L  P  S  F  Q  I 1610      1620      1630      1640      1650      1660      1670      1680      1690      1700
TCCCTGTTTCCCCCCACATCTATACCAGCATCAGCTGGGCTGCTGCCCCTACCACCACCTCCTCCCTCTCTCCGGTCCGAAGCCGCTCTCTCAGCTTCAG
  P  V  S  P  H  I  Y  T  S  I  S  W  A  A  A  P  T  T  T  S  S  L  S  P  V  R  S  R  S  L  S  F  S 1710      1720      1730      1740      1750      1760      1770      1780      1790      1800
CGAGCCCCAGCAGCCGCCACCTACAGTGAAGTCTCACCTCATTGTCACCTCCCCACCCCGTCCTCAGAGCAGCACCAGGAAAGCCCGTGGAGAGGCCAAG
  E  P  Q  Q  P  P  T  V  K  S  H  L  I  V  T  S  P  P  R  A  Q  S  S  T  R  K  A  R  G  E  A  K 1810      1820      1830      1840      1850      1860      1870      1880      1890      1900
AAGTGCCGTAAGGTGTACGGCATCGAGCACCGGGACCACTGGTGCACAGCCTGCCGGTGGAAGAAGGCCTGCCAGCGCTTCCTGGACTGAGCCTGCCTCA
  K  C  R  K  V  Y  G  I  E  H  R  D  Q  W  C  T  A  C  R  W  K  K  A  C  Q  R  F  L  D 1910      1920      1930      1940      1950      1960      1970      1980      1990      2000
CTAGCCCCGCTTCTCACCCTGCCTGGCAGCCGGGAAGCCTCCAGGCCTGCAGCCATCAGCAGAACACAGGGAGATGATGTGGCGTGGATGTGGGCAGCTG 2010      2020      2030      2040      2050      2060      2070      2080      2090      2100
GGGCTCCATTGGCTAAGATAGAACACTTAAAAACACTTTTCTCCCCCTTGTTGGGAGTGCTTTATTTTTTAAAAGCAAACCTAAATGAAACTATTTTTCC 2110      2120      2130      2140      2150      2160      2170      2180      2190      2200
CCTTAAAATAGGAGAGAGCCAAAATTGACCAAGGGTATTCTGCAGCGAACCGGAGACCAAAGAGTTACCCCTACCCCTACCCCATTCCACCCTCTCTGGG 2210      2220      2230      2240      2246
ACTACATATGCATCAAGAGTAGCACAGGATGCTGCCTTGCCTGGTT
```

FIG.5

```
MLSRRLGKRSLLGARVLGPSAAEVPSGATLPLEPQIEVPEGAMSLSPLTS  50
-------------------------------------------------   0

KDPVCQEQPKELLKALGTSGHPQVAFQPGQKVCVWYGGQECKGLVEQHSW 100
-------------------------------------------------   0

AEDKVTVRLLDQKLQIRCKVEEVWLAELQGSASHVPALEPGAQVPAYRPV 150
------------DQKLQVCCRVEEVWLAKLQGPCPQAPPLEPGAQALAYRPV 40

SRNIDVPKRKSDAVEMDEMMAAMVLTSLSCSPVVQSPPGAEPIFSVSRAA 200
SRNIDVPKRKSDAVEMDEMMAAMVLTSLSCSPVVQSPPGTEANFSASRAA  90

CGDPWKESGDVSDSGSS--GHWSGSSGSSTPSPPHPQASPKYLGDAFGS 247
C-DPWKESGDISDSGSSTTSGHWSGSSGVSTPSPPHPQASPKYLGDAFGS 139

PQTDHGFETDPDPFLLDEPAPRKRRNSVKVMYKCLWPSCGKVLRSIVGIK 297
PQTDHGFETDPDPFLLDEPAPRKRKKNSVKVMYKCLWPNCGKVLRSIVGIK 189

RHVKALHLGDTVDSDQFKREEDFYYTEMQMKEESAQAVAAP---PAPGT 343
RHVKALHLGDTVDSDQFKREEDFYYTEVQLKEESAAAAAAAGTPVPGT 239

PMGEPASTSRVTSPSLAALSLPPAKVQSSGPEHPGLESSLPSVALSKSAP 393
PTSEPAPTPSMTGLPLSALPPPLHKAQSSGPEHPGPESSLPSGALSKSAP 289

GSFWHIQADHAYQALPSFQIPVSPHIYTSISWAAAAPTTTSISLSPVRSRSL 443
GSFWHIQADHAYQALPSFQIPVSPHIYTSVSWAAAAPSAACSLSPVRSRSL 339

SFSEPQQPPPTVKSHLIVTSPPRAQSSTRKARGEAKKCRKVYGIEHRDQW 493
SFSEPQQPAPAMKSHLIVTSPPRRAQSGARKARGEAKKCRKVYGIEHRDQW 389

CTACRWKKACQRFLD 508
CTACRWKKACQRFLD 404
```

TRANSCRIPTION FACTOR POLYPEPTIDE THAT REGULATES CHONDROMODULIN-I EXPRESSION

This application is a 371 of PCT/JP00/08257, filed Nov. 24, 2000.

FIELD OF THE INVENTION

The present invention relates to a novel transcription factor, its DNA, recombinant vector, transformant, a method of manufacturing the same or an antibody thereof, or its use.

BACKGROUND ART

In eukaryotic cells, transcription of gene is regulated, as the amount transcription, by interaction between sequences (cis-elements) on chromosomes such as promoters, enhancers, etc. and transcription factors binding thereto. A promoter is composed of the core (basic) sequence comprising TATA box and transcription start site, and the gene-specific expression regulatory region. Regulatory transcription factors bound to the expression regulatory region activate RNA polymerase II holoenzymes (complexes of RNA polymerase II and basal transcription factors) to promote gene transcription. The basal transcription factors bound to the core sequence are engaged in the transcription of many genes and are not specific to genes.

On the other hand, in regulatory transcription factors bound to the expression regulatory region, cells are activated when the cells proliferate or differentiate or respond to the external stimulations such as hormones, cytokines, etc., thus promoting the transcription of genes given. For this reason, regulatory transcription factors are also called gene-specific transcription factors. It is predicted that about 30,000 kinds of gene-specific transcription factors would be present in human and are expected to become drug targets, like receptors on cell surfaces (Mol. Med. Today, 358, 1998).

Human chondromodulin-I (hereinafter sometimes abbreviated as ChM-I) was purified and cloned from bovine fetal epiphyseal cartilage by Hiraki et al. (Biochem. Biophys. Res. Commun., 175:371, 1991), as a factor for promoting DNA synthesis of chondrocytes. Purified ChM-I weakly promoted DNA synthesis of chondrocytes and its activity was potentiated in the presence of bFGF. It was also shown that ChM-I promotes proteoglycan synthesis as well. It became clear from the cDNA sequence that ChM-I was synthesized as a precursor composed of 335, amino acids and mature type was composed of the C-terminal 121 amino acids. This mature ChM-I coincided with the 18-kDa glycoprotein, physiological functions of which are unknown and which P. J. Neame et al. (J. Biol. Chem., 265:9628-9633, 1990) purified from bovine septonasal cartilage and determined its partial amino acid sequence. It was also revealed by the Northern blot analysis that expression of bovine ChM-I was specific to cartilage. Subsequently, it is reported that ChM-I possesses a colony formation promoting activity of chondrocytes (Biochem. Biophys. Res. Commun., 241: 395, 1997), a vascular endothelial cell growth inhibitory action (J. Biol. Chem., 272:32419, 1997, FEBS Letters, 415:321, 1997), a growth promoting/differentiation inhibitory action (FEBS Letters, 406:310, 1997), etc. In growth plate cartilages, ChM-I is expressed in the avascular proliferating cartilage zone, etc. It is thus considered that ChM-I would promote cartilage proliferation and matrix production, vascular invasion would be prevented, and the replacement of cartilage would be controlled by bone (J. Biol. Chem., 272:32419, 1997). As such, ChM-I is a factor for controlling the differentiation and proliferation of cartilage having an anti-angiogenic activity.

During endochondral ossification, chondrocytes in the growth plate cartilage continue to be differentiated in the order of resting cartilage, proliferating cartilage, hypertrophic cartilage and then calcified cartilage and, by vascular invasion, osteoblasts are supplied and then replaced by bone. Further in the course of healing bone fracture, chondrocytes appear after inflammatory reaction and bone fracture is restored via a similar pathway. Thus, the differentiation and proliferation of chondrocytes are clearly important for the process of healing osteopathy or chondropathy.

Suzuki et al. clarified the sequence of human ChM-I gene and described the application of human ChM-I protein to drugs for the treatment of bone fracture, various cartilage-associated diseases, tumors including cancer, etc., because human ChM-I protein possesses a cartilage proliferating action and vascular endothelial cell growth inhibition (Japanese Patent Laid-Open Application No. 7-138295). However, the controlled expression of ChM-I gene remains unclear not been made clear.

Regulatory transcription factors regulate the activity, expression and stability, and enable to develop novel pharmaceuticals useful for the prevention and treatment of various diseases associated with the activity, expression and stability, e.g., joint diseases such as arthritis deformans, chronic articular rheumatism, etc., osteopathy such as bone fracture, etc., and cancer, etc. It has thus been desired in the art to find a new regulatory transcription factor and develop a method of manufacturing the same in a large scale.

DISCLOSURE OF THE INVENTION

In order to solve the foregoing problems, the present inventors have made extensive studies and as a result, have found a novel regulatory transcription factor bound to the promoter of ChM-I gene. Based on these findings, the inventors have made further investigations and come to accomplish the present invention.

That is, the present invention provides the following features.

(1) A polypeptide containing the same or substantially the same amino acid sequence as that represented by SEQ ID NO:5, or its salt.

(2) The polypeptide or its salt according to (1), wherein substantially the same amino acid sequence as that represented by SEQ ID NO:5 is the amino acid sequence represented by SEQ ID NO:19.

(3) The polypeptide or its salt according to (1), which contains the same, or substantially the same amino acid sequence as that represented by SEQ ID NO:4.

(4) The polypeptide or its salt according to (1), wherein substantially the same amino acid sequence as that represented by SEQ ID NO:4 is the amino acid sequence represented by SEQ ID NO:7.

(5) A DNA containing a DNA bearing a base sequence encoding the polypeptide according to (1).

(6) A recombinant vector containing the DNA according to (5).

(7) A transformant transformed with the recombinant vector according to (6).

(8) A method of manufacturing the polypeptide or its salt according to (1), which comprises culturing the transformant according to (7) to produce the polypeptide according to (1).

(9) An antibody to the polypeptide or its salt according to (1).

(10) A diagnostic agent comprising the antibody according to (9).

(11) A method of screening a compound or its salt that promotes or inhibits the activity of the polypeptide or its salt according to (1), which comprises using the polypeptide or its salt according to (1), the DNA according to (5), or the transformant according to (7).

(12) A kit for screening a compound or its salt that promotes or inhibits the activity of the polypeptide or its salt according to (1), comprising the polypeptide or its salt according to (1), the DNA according to (5), or the transformant according to (7).

(13) A compound or its salt that promotes or inhibits the polypeptide or its salt according to (1), which is obtainable using the screening method according to (11) or the screening kit according to (12).

(14) A pharmaceutical comprising a compound or its salt that promotes or inhibits the polypeptide or its salt according to (1), which is obtainable using the screening method according to (11) or the screening kit according to (12).

(15) The pharmaceutical according to (14), which is for the treatment/prevention of chronic rheumatoid arthritis, arthrosis deformans, osteoporosis, bone fracture, cancer, intervertebral disk hernia, sciatica or ectopic chondrogenesis.

(16) A method of screening a compound or its salt that promotes or inhibits the expression of a DNA encoding the polypeptide according to (1), which comprises culturing a cell capable of producing the polypeptide or its salt according to (1) in the presence of a test compound, and assaying the amount of mRNA encoding the polypeptide according to (1) using a DNA encoding the polypeptide according to (1) or its complementary DNA, or a partial DNA thereof.

(17) A compound or its salt that promotes or inhibits the expression of a DNA encoding the polypeptide according to (1), which is obtainable using the screening method according to (16).

(18) A pharmaceutical comprising a compound or its salt that promotes or inhibits the expression of a DNA encoding the polypeptide according to (1), which is obtainable using the screening method according to (16).

(19) The pharmaceutical according to (18), which is for the treatment/prevention of chronic rheumatoid arthritis, arthrosis deformans, osteoporosis, bone fracture, cancer, intervertebral disk hernia, sciatica or ectopic chondrogenesis.

The present invention further provides the following:

(20) An agent comprising the polypeptide or its salt according to (1).

(21) A pharmaceutical comprising the polypeptide or its salt according to (1).

BRIEF DESCRIPTION OF THE DRAWINGS

FIG. 1 shows the base sequence of human ChM-I promoter, wherein the upper and lower columns designate the sequence obtained in EXAMPLE 1 (SEQ ID NO: 14) and the sequence described (SEQ ID NO: 28) in Japanese Patent Laid-Open Application No. 7-138295, respectively.

FIG. 3 shows the DNA sequence (SEQ ID NO: 3) and amino acid sequence (SEQ ID NO: 4) of human-derived regulatory transcription factor gene.

FIG. 4 shows the DNA sequence (SEQ ID NO: 6) and amino acid sequence (SEQ ID NO: 7) of mouse-derived regulatory transcription factor gene.

FIG. 5 shows comparison of amino acid sequence between the human-derived regulatory transcription factor (SEQ ID NO: 4) and the mouse-derived regulatory transcription factor (SEQ ID NO: 7).

BEST MODE OF EMBODIMENT OF THE INVENTION

Figure 2:
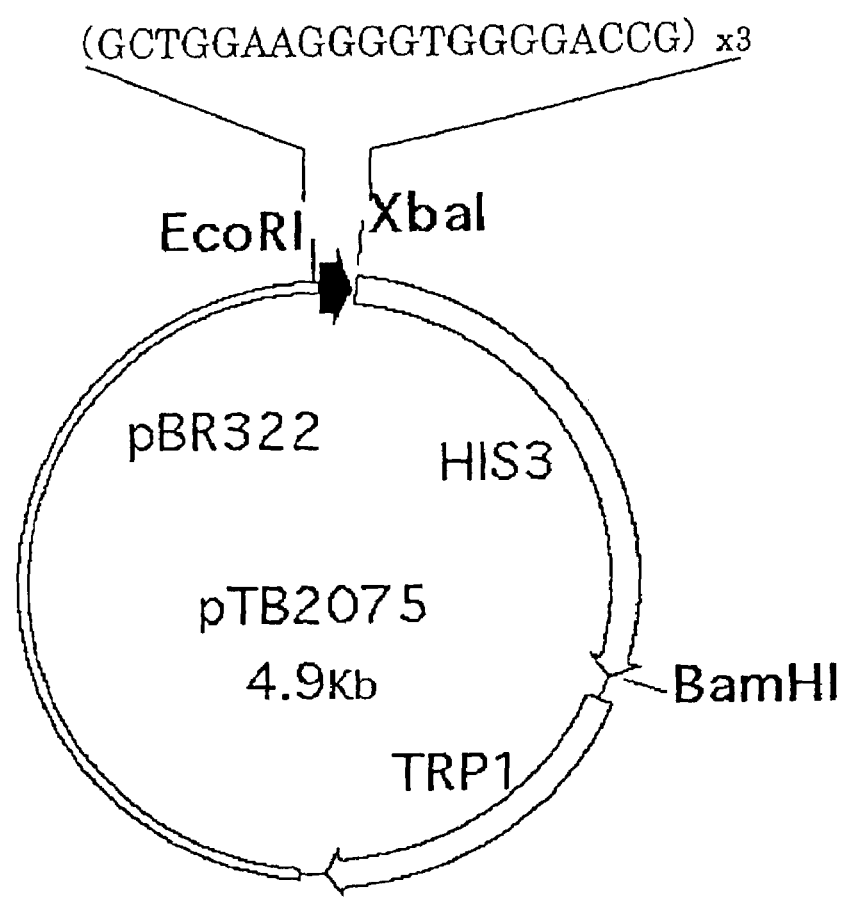
FIG. 2 shows a schematic view of plasmid pTB2075 that includes (SEQ ID NO: 29).

The polypeptides of the present invention containing the amino acid sequence shown by SEQ ID NO:5 (hereinafter sometimes referred to as human type polypeptides), the polypeptides containing the amino acid sequence shown by SEQ ID NO:19 (hereinafter sometimes referred to as mouse type polypeptides), and the polypeptides containing substantially the same amino acid sequence as in the human type polypeptides (hereinafter the human type polypeptides, mouse type polypeptides and polypeptides containing substantially the same amino acid sequences as in the human type polypeptide are sometimes collectively referred to as the polypeptides of the present invention), may be any polypeptides derived from any cells of human and other warm-blooded animals (e.g., guinea pig, rat, mouse, chicken, rabbit, swine, sheep, bovine, monkey, etc.), e.g., liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell or interstitial cell, etc., or, the corresponding precursor cells, stem cells, cancer cells, etc., or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, cartilage, joint, skeletal muscle, etc.; the polypeptides may also be recombinant polypeptides or synthetic polypeptides.

The amino acid sequence which has substantially the same amino acid sequence as the amino acid sequence represented by SEQ ID NO:5 includes an amino acid sequence having at least about 50% homology, preferably at least about 60% homology, more preferably at least about 70% homology, much more preferably at least about 80% homology, further much more preferably at least about 90% homology, and most preferably at least about 95% homology, to the amino acid sequence represented by SEQ ID NO:5.

Specific examples of substantially the same amino acid sequence as the amino acid sequence shown by SEQ ID NO:5 include an amino acid sequence represented by e.g., SEQ ID NO:19, and the like.

Specific examples of the polypeptide which has the same amino acid sequence or substantially the same amino acid sequence as the amino acid sequence shown by SEQ ID NO:5 include polypeptides containing the same or substantially the same amino acid sequence as the amino acid sequence represented by, e.g., SEQ ID NO:4, and the like.

The amino acid sequence which has substantially the same amino acid sequence as the amino acid sequence represented by SEQ ID NO:4 includes an amino acid sequence having at least about 50% homology, preferably at least about 60% homology, more preferably at least about 70% homology, much more preferably at least about 80% homology, further much more preferably at least about 90% homology, and most preferably at least about 95% homology, to the amino acid sequence represented by SEQ ID NO:4.

Specific examples of substantially the same amino acid sequence as the amino acid sequence shown by SEQ ID NO:4 include an amino acid sequence represented by, e.g., SEQ ID NO:7, and the like.

Preferred examples of the polypeptide which has substantially the same amino acid sequence as the amino acid sequence represented by SEQ ID NO:4, include a polypeptide having substantially the same amino acid sequence as the amino acid sequence represented by e.g., SEQ ID NO:4 and having the activity substantially equivalent to that of the amino acid sequence represented by SEQ ID NO:4. Specific examples of such polypeptides include a polypeptide having the amino acid sequence shown by SEQ ID NO:7, and the like.

Preferred examples of the polypeptide which has substantially the same amino acid sequence as the amino acid sequence represented by SEQ ID NO:5 include a polypeptide having substantially the same amino acid sequence as the amino acid sequence represented by, e.g., SEQ ID NO:5 and having the activity substantially equivalent to that of the amino acid sequence represented by SEQ ID NO:5. Specific examples of such polypeptides include a polypeptide having the amino acid sequence shown by SEQ ID NO:19, and the like.

The substantially equivalent activity refers to, e.g., activities as regulatory transcription factors, etc. The substantially equivalent is used to mean that the nature of these activities is equivalent qualitatively. Therefore, it is preferred that the these activities such as binding to the ChM-I gene promoter, transcription regulation, etc. are equivalent in strength (e.g., about 0.1 to about 100 times, preferably about 0.5 to about 10 times, more preferably about 0.5 to about 2 times), and even differences among grades such as the strength of these activities and molecular weight of the polypeptide are allowable.

More specifically, the polypeptides containing substantially the same amino acid sequence as the amino acid sequence shown by SEQ ID NO:4 or SEQ ID NO:5 include so-called muteins such as polypeptides containing 1) an amino acid sequence represented by SEQ ID NO:4 or SEQ ID NO:5, of which 1 or at least 2 (preferably approximately 1 to 30, more preferably approximately 1 to 10 and most preferably several (1 to 5)) amino acids are deleted; 2) an amino acid sequence represented by SEQ ID NO:4 or 5, to which 1 or at least 2 (preferably approximately 1 to 30, more preferably approximately 1 to 10 and most preferably several (1 to 5)) amino acids are added; 3) an amino acid sequence represented by SEQ ID NO:4 or 5, into which 1 or at least 2 (preferably approximately 1 to 30, more preferably approximately 1 to 10 and most preferably several (1 to 5)) amino acids are inserted, 4) an amino acid sequence represented by SEQ ID NO:4 or 5, in which 1 or at least 2 (preferably approximately 1 to 30, more preferably approximately 1 to 10 and most preferably several (1 to 5)) amino acids are substituted by other amino acids; and 5) a mutein, a polypeptide, which has a combination of the above amino acid sequences.

When an amino acid sequence(s) are inserted, deleted or substituted as described above, the positions of such insertion, deletion or substitution are not particularly limited, but include specifically 1) positions other than the amino acid sequences common to the amino acid sequences represented by SEQ ID NO:4 and SEQ ID NO:7, respectively; 2) positions other than the amino acid sequences common to the amino acid sequences represented by SEQ ID NO:4 and SEQ ID NO:5, respectively; and the like.

Throughout the present specification, the polypeptides are represented in accordance with the conventional way of describing polypeptides, that is, the N-terminus (amino terminus) at the left hand and the C-terminus (carboxyl terminus) at the right hand. In the polypeptides of the present invention including the polypeptide containing the amino acid sequence shown by SEQ ID NO:5, the C-terminus is usually in the form of a carboxyl group (—COOH) or a carboxylate (—COO$^-$) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like which is used widely as an ester for oral administration may also be used.

Where the polypeptide of the present invention contains a carboxyl group (or a carboxylate) at a position other than the C-terminus, it may be amidated or esterified and such an amide or ester is also included within the polypeptide of the present invention. The ester group may be the same group as that described with respect to the above C-terminal.

Furthermore, examples of the polypeptide of the present invention include variants of the above polypeptides, wherein the amino group at the N-terminus (e.g., methionine residue) of the polypeptide is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains.

The polypeptides of the present invention or salts thereof may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide or salts thereof may be manufactured from human or other warm-blooded animal cells or tissues by a publicly known method of purifying a polypeptide (protein), or may be manufactured by culturing a transformant containing a DNA encoding the polypeptide, as will be later described. They may also be manufactured by modifications of peptide synthesis described hereinafter.

Where the polypeptides or salts are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the polypeptide of the present invention, its salts or amides, commercially available resins that are used for polypeptide (protein) synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide (protein) condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide (protein) binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower $C_{1-6}$ alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptide, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group in the peptide chain has been eliminated and a polypeptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide or its amide.

To prepare the esterified polypeptide, for example, the α-carboxyl group of the carboxy terminal amino acid is condensed with a desired alcohol to prepare the amino acid ester, which is followed by procedure similar to the preparation of the amidated polypeptide above to give the desired esterified polypeptide.

The polypeptide or salts of the present invention can be manufactured by publicly known methods for peptide synthesis. For the methods for peptide synthesis, for example, either solid phase synthesis or liquid phase synthesis may be used. That is, the partial peptide or amino acids that can construct the partial peptide of the present invention are condensed with the remaining part. Where the product contains protecting groups, these protecting groups are removed so that the desired peptide can be manufactured Publicly known methods for condensation and elimination of the protecting groups are described in 1)-5) below.
1) M. Bodanszky & M. A. Ondetti: Peptide Synthesis, Interscience Publishers, New York (1966)
2) Schroeder & Luebke: The Peptide, Academic Press, New York (1965)
3) Nobuo Izumiya, et al.: *Peptide Gosei-no-Kiso to Jikken* (Basics and experiments of peptide synthesis), published by Maruzen Co. (1975)
4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)
5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the polypeptide of the present invention. When the polypeptide obtained by the above methods is in a free form, the polypeptide can be converted into an appropriate salt by a publicly known method; when the polypeptide is obtained in a salt form, it can be converted into a free form or a different salt form by a publicly known method.

The DNA encoding the polypeptide of the present invention may be any DNA so long as it contains the base sequence encoding the polypeptide of the present invention described above. Such a DNA may also be any one of genomic DNA, cDNA derived from the cells or tissues described above and synthetic DNA.

The vector to be used for the library may be any of bacteriophage, plasmid, cosmid, phagemid and the like. In addition, the DNA can be directly amplified by reverse transcriptase polymerase chain reaction (hereinafter abbreviated as RT-PCR) with total RNA or mRNA fraction prepared from the above-described cells or tissues.

Specifically, the DNA encoding the polypeptide of the present invention may be any one of, for example, DNA containing the base sequence represented by SEQ ID NO:18, or any DNA having a base sequence hybridizable to the base sequence represented by SEQ ID NO:18 under high stringent conditions, having a DNA encoding a polypeptide which has the activities substantially equivalent to those of the polypeptide of the present invention (e.g., an immunogenicity, etc.), and encoding a polypeptide which has the activities substantially equivalent to those of the polypeptide of the present invention.

Specific examples of the DNA containing the base sequence represented by SEQ ID NO:18 are DNA containing the base sequence represented by SEQ ID NO:3, and the like.

Specific examples of the DNA that is hybridizable to the base sequence represented by SEQ ID NO:18 under high stringent conditions include DNA having at least about 60% homology, preferably at least about 70% homology and most preferably at least about 80% homology, to the base sequence represented by SEQ ID NO:18.

Specifically, the DNA that is hybridizable to a DNA having the base sequence represented by SEQ ID NO:18 under high stringent conditions includes a DNA containing the base sequence represented by SEQ ID NO:18, or a DNA having a base sequence hybridizable to the base sequence represented by SEQ ID NO:18 under high stringent conditions, having a DNA encoding a polypeptide which has the activities substantially equivalent to those of the polypeptide of the present invention (e.g., a transcription regulatory activity, binding to the ChM-I gene promoter, etc.), and encoding a polypeptide which has the activities substantially equivalent to those of the polypeptide of the present invention (e.g., DNA containing the base sequence represented by SEQ ID NO:3, SEQ ID NO:6 or SEQ ID NO:20).

The hybridization can be carried out by publicly known methods or by a modification thereof, for example, according to the method described in Molecular Cloning, 2nd. (J. Sambrook et al., Cold Spring Harbor Lab. Press, 1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM at a temperature of about 50° C. to about 70° C., preferably about 60° C. to about 65° C.

More specifically, as the DNA encoding the polypeptide having the amino acid sequence represented by SEQ ID NO:4, there may be employed DNA having the 1-1212 base sequence in the base sequence represented by SEQ ID NO:3, etc.; DNA having the base sequence represented by SEQ ID NO:18 may be used as the DNA encoding the polypeptide of the present invention having the amino acid sequence represented by SEQ ID NO:5; a DNA having the base sequence represented by SEQ ID NO:18 may be employed as the DNA encoding the polypeptide having the amino acid sequence represented by SEQ ID NO:5; a DNA having the 364-1887 base sequence in the base sequence represented by SEQ ID NO:6 may be used as the DNA encoding the polypeptide of the present invention having the amino acid sequence represented by SEQ ID NO:7; and as the DNA encoding the polypeptide of the present invention having the amino acid sequence represented by SEQ ID NO:19, there may be employed a DNA having the base sequence represented by SEQ ID NO:20, and the like.

For cloning of the DNA that completely encodes the polypeptide of the present invention, the DNA may be either amplified by publicly known PCR using synthetic DNA primers containing a part of the base sequence of a DNA encoding the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Conversion of the base sequence of DNA can be effected by publicly known methods such as the ODA-LA PCR method, the Gapped duplex method or the Kunkel method or its modification by using a publicly known kit available as Mutan™-Super Express Km or Mutan™-K (both by Takara Shuzo Co., Ltd.).

The cloned DNA encoding the polypeptide can be used as it is, depending upon purpose or, if desired, after digestion with a restriction enzyme or after addition of a linker thereto: The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, β-actin, etc.

Among them, CMV (cytomegalovirus) promoter or SRα promoter is preferably used. Where the host is bacteria of the genus *Escherichia*, preferred examples of the promoter include trp promoter, lac promoter, recA promoter, $\lambda P_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, Geneticin resistance), etc. In particular, when dhfr gene is used as the selection marker using dhfr gene-deficient Chinese hamster cells, recombinants may also be selected on thymidine free media.

If necessary, a signal sequence that matches with a host is added to the N-terminus of the polypeptide of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the polypeptide of the present invention thus constructed, transformants can be manufactured.

As the host, there may be employed, e.g., bacteria belonging to the genus *Escherichia*, bacteria belonging to the genus *Bacillus*, yeast, insect cells, insects, animal cells, and the like.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [(Gene, 24, 255 (1983)), 207-21 [Journal of Biochemistry, 95, 87 (1984)], etc.

Examples of yeast include *Saccharomyces Cerevisiae* AH22, AH22R$^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In Vivo, 13, 213-217 (1977).

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO (dhfr$^-$) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's, Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the polypeptide of the present invention can be produced in the cell membrane of the transformant, etc.

The polypeptide of the present invention can be separated and purified from the culture described above by the following procedures.

When the polypeptide of the present invention is extracted from the culture or cells, after cultivation the transformant or cell is collected by a publicly known method and suspended in a appropriate buffer. The transformant or cell is then disrupted by publicly known methods such as ultrasonication, a treatment with lysozyme and/or freeze-thaw cycling, followed by centrifugation, filtration, etc. Thus, the crude extract of the polypeptide or its partial peptide of the present invention can be obtained. The buffer used for the procedures may contain a protein modifier such as urea or guanidine hydrochloride, or a surfactant such as Triton X-100™, etc. When the polypeptide or its partial peptide of the present invention is secreted in the culture broth, after completion of the cultivation the supernatant can be separated from the transformant or cell to collect the supernatant by a publicly known method.

The supernatant or polypeptide contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein modifying enzyme or proteinase so that the polypeptide can be appropriately modified to partially remove the polypeptide. Examples of these enzymes include trypsin, chymotrypsin, arginyl endopeptidase, protein kinase, glycosidase, and the like.

The activity of the thus produced polypeptide of the present invention or salts thereof can be determined by an enzyme immunoassay using a specific antibody, Western blot analysis, etc.

Antibodies to the polypeptide of the present invention or salts thereof may be any of polyclonal antibodies and monoclonal antibodies, as long as they are capable of recognizing the polypeptide of the present invention or salts thereof.

The antibodies to the polypeptide of the present invention or salts thereof may be manufactured by publicly known methods for manufacturing antibodies or antisera, using as antigens the polypeptide of the present invention.

[Preparation of Monoclonal Antibody]

(a) Preparation of Monoclonal Antibody-Producing Cells

The polypeptide or its salt of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion promoter are polyethylene glycol (PEG), Sendai virus, etc.; among them, PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the polypeptide as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0:1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNA having a complementary or substantial complementary base sequence to the DNA encoding the polypeptide of the present invention (hereinafter sometimes referred to as the DNA of the present invention) can be any antisense DNA so long as it possesses a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). Particularly in the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence, which encodes the N-terminal region of the polypeptide of the present invention, is preferable. These antisense DNAs can be synthesized using a publicly known DNA synthesizer, etc.

Hereinafter the utilities of the polypeptide of the present invention or salts thereof (hereinafter sometimes referred to as the polypeptide of the present invention); the DNA encoding the polypeptide of the present invention (hereinafter sometimes referred to as the DNA of the present invention), the transformant transformed by recombinant vector containing the DNA encoding the polypeptide of the present invention (hereinafter sometimes referred to as the transformant of the present invention), antibodies to the polypeptide of the present invention or salts thereof (hereinafter sometimes referred to as the antibody of the present invention) and the antisense DNA will be described.

(1) Therapeutic/Prophylactic Agent for the Diseases with which the Polypeptide of the Present Invention is Associated The polypeptide of the present invention binds to promoters of the ChM-I gene to promote the transcription of the gene and promote the expression of type II collagen gene. Thus, it is likely that any abnormality or deficiency in the DNA encoding the polypeptide of the present invention would cause a variety of diseases such as chronic rheumatoid arthritis, arthrosis deformans, osteoporosis, bone fracture, cancer, etc.

Therefore, the polypeptide of the present invention can be used as pharmaceuticals for the treatment/prevention of various diseases, e.g., chronic rheumatoid arthritis, arthrosis deformans, osteoporosis, bone fracture, cancer, etc.

When a patient has a reduced level of, or is deficient of the polypeptide of the present invention in vivo, the DNA of the present invention can provide the role of the polypeptide of the present invention sufficiently or properly for the patient, (a) by administering the DNA of the present invention to the patient to express the polypeptide of the present invention in vivo, (b) by inserting the DNA of the present invention into a cell, expressing the polypeptide of the present invention and then transplanting the cell to the patient, or (c) by administering the polypeptide of the present invention to the patient; etc.

Where the DNA of the present invention is used as the prophylactic/therapeutic agents described above, the DNA per se is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as naked DNA, or with adjuvants to assist its uptake by gene gun or through a catheter such as a catheter with a hydrogel.

Where the polypeptide of the present invention is used as the aforesaid therapeutic/prophylactic agents, the polypeptide is advantageously used on a purified level of at least 90%, preferably at least 95%, more preferably at least 98% and most preferably at least 99%.

The polypeptide of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™, HCO-50, etc.), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention has been inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, chicken, sheep, swine, bovine, horse, cat, dog, monkey, chimpanzee, etc.).

The dose of the polypeptide of the present invention varies depending on target disease, subject to be administered, route for administration, etc.; for example, in oral administration for the treatment of chronic rheumatoid arthritis, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc., but it is advantageous for the treatment of chronic rheumatoid arthritis to administer the polypeptide pf the present invention intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of Drug Candidate Compounds for Diseases

Because the polypeptide of the present invention possesses the activity of promoting the transcription of the ChM-I gene and the activity of promoting the expression of the type II collagen gene, a compound or its salts that promote the activities (e.g., the binding activity to the ChM-I gene promoter, the transcription activity of the ChM-I gene, the activity of promoting the expression of the type II collagen gene, etc.) of the polypeptide of the present invention can be used as drugs for the treatment/prevention of diseases such as chronic rheumatoid arthritis, arthrosis deformans, osteoporosis, bone fracture, cancer, etc.

On the other hand, a compound or its salts that inhibit the activities of the polypeptide of the present invention can be used as the therapeutic/prophylactic agent for intervertebral disk hernia, sciatica, ectopic chondrogenesis, etc.

Therefore, the polypeptide of the present invention is useful as reagents for screening the compound or its salts that promote or inhibit the activities of the polypeptide of the present invention.

That is, the present invention provides:

1) a method for screening the compound or its salts that promote the activities of the polypeptide of the present invention (hereinafter sometimes merely referred to as the promoter), or the compound or its salts that inhibit the activities of the polypeptide of the present invention (hereinafter sometimes merely referred to as the inhibitor), characterized by using the polypeptide of the present invention.

More specifically, the present invention provides:

2) a method for screening the promoting agent or the inhibitor, which comprises comparing:

(i) the case in which a DNA containing the cis-element of the ChM-I gene promoter is brought into contact with the polypeptide of the present invention, and (ii) the case in which a DNA containing the cis-element of the ChM-I gene promoter and a test compound are brought into contact with the polypeptide of the present invention.

Specifically, the screening method described above is characterized by comparing the amounts of the polypeptide of the present invention bound to the ChM-I gene promoter in the cases (i) and (ii).

The DNA containing the cis-element of the ChM-I gene promoter is preferably used in its labeled form using, e.g., a radioisotope, a pigment, etc. Examples of the radioisotope used are $^{32}P$, $^{3}H$, etc. and examples of the pigment are fluorescent pigments such as fluorescein, FAM (manufactured by PE Biosystems), JOE (manufactured by PE Biosystems), TAMRA (manufactured by PE Biosystems), ROX (manufactured by PE Biosystems), Cy5 (manufactured by Amersham), Cys (manufactured by Amersham), etc. Examples of the DNA containing the cis-element of the ChM-I gene promoter include single stranded or double stranded DNA containing the sequence composed of at least 6 consecutive bases (preferably 6 to 20, more preferably 8 to 20 and most preferably 10 to 20) in the same or substantially the same base sequence as the base sequence shown by SEQ ID NO:17. The DNA can be prepared by a publicly known chemical synthesis method.

Examples of substantially the same base sequence as the base sequence shown by SEQ ID NO:17 are base sequences in which approximately 1 to 3 bases in the base sequence shown by SEQ ID NO:17 are replaced by other bases. Specific examples include the base sequence shown by SEQ ID NO:21 (Japanese Patent Laid-Open Application No. 7-138295), and the like.

The amount of the polypeptide of the present invention to the DNA containing the cis-element of the ChM-I gene promoter can be quantitatively determined by measuring the DNA containing the cis-element of the ChM-I gene promoter bound to the polypeptide of the present invention in terms of, e.g., the activity of the labeled DNA. The measurement can be made in accordance with a publicly known method, e.g., the gel shift assay method (SHIN IDENSHI KOGAKU HANDBOOK (New Genetic Engineering Handbook), 3rd revised version, edited by Masami Muramatsu, et al., published by Yodosha Publishing Co., page 150, 1999).

Examples of test compounds are a peptide, a protein, a non-peptide compound, a synthetic compound, a fermentation product, a cell extract, a plant extract, an animal tissue extract and the like. These compounds may be novel compounds or publicly known compounds.

The present invention further relates to a method for screening the promoting agent or the inhibitor, characterized by using the DNA of the present invention or the DNA of the present invention. Specifically, the present invention provides a method for screening the promoting agent or the inhibitor, which comprises culturing the DNA of the present invention and yeast (e.g., Saccharomyces cerevisiae) transformed by a DNA ligated with a reporter gene at the downstream of the cis-element of the ChM-I gene promoter in the presence or absence of a test compound, detecting and comparing the expression of the reporter gene.

As the reporter gene, there may be employed, e.g., a gene compensating for auxotrophy such as HIS3, TRP1, URA3, etc., a chemical resistant gene such as aureobasidin, etc., a stain marker gene such as lacZ (β-galactosidase gene), etc.

The compound or its salts that promote or inhibit the activities of the polypeptide of the present invention can be screened, e.g., by transforming yeast having auxotrophy for histidine with the DNA of the present invention and the DNA ligated with HIS3 gene as a reporter gene at the downstream of the cis-element of the ChM-I gene promoter, culturing the resulting transformant in a histidine-free medium in the presence of a test compound and measuring the growth (accelerated or inhibited proliferation) of the transformant. The test compound that promotes the growth of the transformant can be selected as the compound capable of promoting the activities of the polypeptide of the present invention. Likewise the test compound that inhibits the growth of the transformant can be selected as the compound capable of inhibiting the activities of the polypeptide of the present invention.

Also, the compound or its salts that promote or inhibit the activities of the polypeptide of the present invention can be screened by transforming yeast with the DNA of the present invention and the DNA ligated with aureobasidin A-resistant gene as a reporter gene at the downstream of the cis-element of the ChM-I gene promoter, culturing the resulting transformant in a medium containing the test compound and aureobasidin A and measuring the growth (accelerated or inhibited proliferation) of the transformant. The test compound that promotes the growth of the transformant can be selected as the compound capable of promoting the activities of the polypeptide of the present invention. Likewise the test compound that inhibits the growth of the transformant can be selected as the compound capable of inhibiting the activities of the polypeptide of the present invention.

Furthermore, the compound or its salts that promote or inhibit the activities of the polypeptide of the present invention can be screened by transforming yeast with the DNA of the present invention and the DNA ligated with β-galactosidase gene (lacZ) as a reporter gene at the downstream of the cis-element of the ChM-I gene promoter, culturing the resulting transformant in the presence of a test compound and a substrate reagent of β-galactosidase such as 5-bromo-4-chloro-3-indolyl-β-galactopyranoside (X-gal), and measuring the degree of staining of the transformant. When the transformant is stained to a deeper blue in the presence of the test compound than in the absence of the test compound, the test compound can be selected as the compound capable of promoting the activities of the polypeptide of the present invention. Conversely when the transformant is stained to a pale blue or not stained at all, the test compound can be selected as the compound capable of inhibiting the activities of the polypeptide of the present invention.

Furthermore, the amount of the reporter gene product (e.g., mRNA, protein) is measured by a publicly known method, whereby a test compound that increases the amount of the reporter gene product can be selected as the compound capable of inhibiting the activities of the present invention.

Examples of the cis-element of the ChM-I gene promoter used in the screening method described above include DNA containing the sequence composed of at least 6 consecutive bases (preferably 6 to 20, more preferably 8 to 20 and most preferably 10 to 20) in the same or substantially the same base sequence as the base sequence shown by SEQ ID NO:17. Examples of substantially the same base sequence as the base sequence shown by SEQ ID NO:17 are base sequences in which approximately 1 to 3 bases in the base sequence shown by SEQ ID NO:17 are replaced by other bases. Specific examples include the base sequence shown by SEQ ID NO:21 (Japanese Patent Laid Open Application No. 7-138295), and the like.

While there is no particular restriction in the number of bases between the ChM-I gene promoter and translation initiation codon of the reporter gene ligated downstream the ChM-I gene promoter, the number of bases is generally 0 to 100 bases, preferably 10 to 50 bases, and more preferably 10 to 30 bases.

The transformant can be cultured in a manner similar to the culturing of the transformant described hereinabove.

The kit for screening according to the present invention comprises the polypeptide of the present invention, the DNA of the present invention, or the transformant of the present invention. Preferably, the kit for screening of the present invention comprises the polypeptide of the present invention, the DNA of the present invention, or the transformant of the present invention, and the DNA containing the cis-element of the ChM-I gene promoter. In the case of using the transformant of the present invention, a transformant transformed with the DNA of the present invention and the DNA containing the cis-element of the ChM-I gene promoter may be employed as well.

Furthermore, the present invention provides:

1) a method for screening the compound or its salts that promote or inhibit the expression of the DNA encoding the polypeptide of the present invention, characterized by culturing a cell capable of producing the polypeptide of the present invention in the presence of a test compound and measuring the amount of mRNA encoding the polypeptide of the present invention. More specifically, the present invention provides:

2) a method for screening the compound or its salts that promote or inhibit the expression of the DNA encoding the polypeptide of the present invention, characterized by comparing:

(i) the expressed amount of mRNA encoding the polypeptide of the present invention when a cell capable of producing the polypeptide of the present invention is cultured, and, (ii) the expressed amount of mRNA encoding the polypeptide of the present invention when a cell capable of producing the polypeptide of the present invention is cultured in the presence of a test compound.

Examples of the cell capable of producing the polypeptide of the present invention are the transformant of the present invention described above, publicly known warm-blooded animal cells capable of producing ChM-I, and the like. As the warm-blooded animal cells capable of producing ChM-I, there are, e.g., animal cells capable of producing ChM-I in the presence of an expression inducer such as insulin, etc., more specifically, mouse ATDC5 cell, etc.

The cell capable of producing the polypeptide of the present invention may be cultured in a similar manner to the cultivation of the transformant of the present invention described hereinabove. Where animal cells capable of producing ChM-I by contacting with an expression inducer, the animal cells may be cultured in the presence or absence of the expression inducer.

The amount of mRNA encoding the polypeptide of the present invention can be determined by bringing RNA extracted from cells in accordance with a publicly known method in contact with the DNA of the present invention or its complementary DNA, and measuring the amount of mRNA bound to the DNA of the present invention or its complementary DNA. By labeling the DNA of the present invention or its complementary DNA with, e.g., a radioisotopes a pigment, etc., the amount of mRNA encoding the polypeptide of the present invention, which is bound to the DNA of the present invention or its complementary DNA, can be easily assayed. Examples of the radioisotope and the pigment used are the same as used for labeling the DNA containing the cis-element of the ChM-I gene promoter described above.

The amount of mRNA encoding the polypeptide of the present invention can also be determined by converting RNA extracted from cells into cDNA using a reverse transcriptase, and measuring the amount of cDNA amplified by PCR using as a primer the DNA of the present invention or its complementary DNA or its partial DNA.

As the complementary DNA to the DNA of the present invention, which is used to determine the amount of mRNA encoding the polypeptide of the present invention, there is a DNA (lower strand) having a complementary sequence to the DNA (upper strand) of the present invention. Examples of the partial DNA of the DNA of the present invention are base sequences composed of approximately 10 to 2200, preferably approximately 10 to 300, and more preferably approximately 10 to 30, of consecutive bases in the base sequence of the DNA of the present invention. Examples of the partial DNA of the complementary DNA to the DNA of the present invention are DNAs containing sequences complementary to the partial DNA of the DNA of the present invention described above. Particularly preferred examples of the primers used for PCR are DNA having the base sequence represented by SEQ ID NO:8 and DNA having the base sequence represented by SEQ ID NO:9.

The test compound that increases the amount of mRNA encoding the polypeptide of the present invention can be selected as the compound capable of promoting the expression of the DNA of the present invention. Likewise the test compound that decreases the amount of mRNA encoding the polypeptide of the present invention can be selected as the compound capable of inhibiting the expression of the DNA of the present invention.

The compound or its salt obtainable using the screening method or the screening kit of the present invention is the compound selected from the test compounds described above, e.g., peptides, proteins, non-peptide compounds, synthetic compounds, fermentation products, cell extracts, plant extracts, animal tissue extracts, blood plasma, etc. and the compound that promotes or inhibits the activities (e.g., the binding activity to the ChM-I gene promoter, the ChM-I gene transcription activity, the activity of promoting the expression of type II collagen gene, etc.) of the polypeptide of the present invention, or the expression of the DNA of the present invention.

As the salts of the compound, there may be employed similar salts to those of the polypeptide of the present invention described above.

The compound that promotes the activities (e.g., the binding activity to the ChM-I gene promoter, the ChM-I gene transcription activity, the activity of promoting the expression of type II collagen gene, etc.) of the polypeptide of the present invention, or the expression of the DNA of the present invention is available as pharmaceuticals for the treatment/prevention of diseases, e.g., chronic rheumatoid arthritis, arthrosis deformans, osteoporosis, bone fracture, cancer, etc.

On the other hand the compound that inhibits the activities of the polypeptide of the present invention or the expression of the DNA of the present invention is useful as pharmaceuticals for the treatment/prevention of diseases, e.g., intervertebral disk hernia, sciatica, ectopic chondrogenesis, etc.

When the compound obtainable by the screening method or the screening kit of the present invention are used as the therapeutic/prophylactic agents described above, a conventional means may be applied to making pharmaceutical preparations. For example, the compound may be prepared into tablets, capsules, elixirs, microcapsules, sterile solutions, suspensions, etc., in the same manner as in the pharmaceuticals containing the polypeptide of the present invention described above.

Since the thus obtained pharmaceutical preparation is safe and low toxic, it can be administered to human or warm-blooded animal (e.g., mouse, rat, rabbit, sheep, swine, bovine, horse, chicken, cat, dog, monkey, chimpanzee, etc.).

The dose of the compound or salts thereof varies depending on activity, target disease, subject to be administered, route for administration, etc.; for example, when the compound that promotes the activities of the polypeptide of the present invention or the expression of the DNA of the present invention is orally administered for the purpose of treating chronic rheumatoid arthritis, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. but when the compound that promotes the activities of the polypeptide of the present invention or the expression of the DNA of the present invention is parenterally administered to adult (as 60 kg body weight) for the purpose of treating chronic rheumatoid arthritis, it is advantageous to administer the compound intravenously at a daily dose of about 0.01 to about 30 mg, preferably about 0.1 to about 20 mg, more preferably about 0.1 to about 10 mg for. For other animal species, the corresponding dose as converted per 60 kg weight can be administered.

On the other hand, when the compound that inhibits the activities of the polypeptide of the present invention or the expression of the DNA of the present invention is orally administered for the purpose of treating intervertebral disk hernia, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. but when the compound that promotes the activities of the polypeptide of the present invention or the expression of the DNA of the present invention is parenterally administered to adult (as 60 kg body weight) for the purpose of treating intervertebral disk hernia, it is advantageous to administer the compound intravenously at a daily dose of about 0.01 to about 30 mg, preferably about 0.1 to about 20 mg, more preferably about 0.1 to about 10 mg for. For other animal species, the corresponding dose as converted per 60 kg weight can be administered.

Also, the polypeptide of the present invention promotes the transcription of a gene having the cis-element containing the same or substantially the same base sequence as the base sequence represented by SEQ ID NO:17, because the polypeptide specifically binds to the cis-element containing the same or substantially the same base sequence as the base sequence represented by SEQ ID NO:17. Therefore, in addition to the ChM-I gene, the polypeptide of the present invention, the DNA of the present invention or the transformant of the present invention may also be used for screening a compound that promotes or inhibits the transcription of other genes containing the same or substantially the same base sequence as the base sequence represented by SEQ ID NO:17.

(3) Quantification for the Polypeptide of the Present Invention or Salts Thereof:

The antibody to the polypeptide of the present invention is capable of specifically recognizing the polypeptide of the present invention and thus, can be used for a quantification of the polypeptide of the present invention in a test sample fluid, in particular, for a quantification by sandwich immunoassay.

That is, the present invention provides:

(i) a method for quantification of the polypeptide of the present invention in a test sample fluid, which comprises competitively reacting the antibody of the present invention, a test sample fluid and the labeled polypeptide of the present invention, and measuring the ratio of the labeled polypeptide of the present invention bound to said antibody; and, (ii) a method for quantification of the polypeptide of the present invention in a test sample fluid, which comprises reacting the test sample fluid simultaneously or continuously with the antibody of the present invention immobilized on a carrier and a labeled form of another antibody of the present invention, and then measuring the activity of the labeling agent on the insoluble carrier.

In the method (ii) for quantification described above, it is preferred that one antibody is capable of recognizing the N-terminal region of the polypeptide of the present invention, while another antibody is capable of recognizing the C-terminal region of the polypeptide of the present invention.

The monoclonal antibody to the polypeptide of the present invention (hereinafter sometimes referred to as the monoclonal antibody of the present invention) may be used to assay the polypeptide of the present invention. Moreover, the polypeptide of the present invention may be detected by means of a tissue staining, etc. as well. For these purposes, the antibody molecule per se may be used or $F(ab')_2$, Fab' or Fab fractions of the antibody molecule may also be used.

There is no particular limitation for the assaying method using the antibody to the polypeptide of the present invention; any method may be used so far as it is associate with a method in which the amount of antibody, antigen or antibody-antigen complex can be detected by a chemical or a physical means, depending on or corresponding to the amount of antigen (e.g., the amount of protein) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the polypeptide of the present invention in the test sample fluid can be quantified. The first and second reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the polypeptide of the present invention by the sandwich method according to the present invention, preferred monoclonal antibodies of the present invention used for the first and the second reactions are antibodies, which binding sites to the polypeptide of the present invention are different from one another. Thus, the antibodies used in the first and the second reactions are those wherein, when the antibody used in the second reaction recognizes the C-terminal region of the polypeptide of the present invention, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method and nephrometry.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the polypeptide of the present invention may be constructed in addition to conditions or operations conventionally used for each of the methods, taking the technical consideration of one skilled in the art into account consideration. For the details of such conventional technical means, reference may be made to a variety of reviews, reference books, etc.

For the details reference may be made to, for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay"

(Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.

As described above, the polypeptide of the present invention can be quantified with high sensitivity, using the antibody of the present invention.

Furthermore, by quantifying the level of the polypeptide of the present invention using the antibody of the present invention, 1) when a decreased level of the polypeptide of the present invention is detected, it can be diagnosed that diseases such as chronic rheumatoid arthritis, arthrosis deformans, osteoporosis, bone fracture, cancer, etc. are involved or it is highly likely to suffer from these disease in the future; and 2) when an increased level of the polypeptide of the present invention is detected, it can be diagnosed that diseases such as intervertebral disk hernia, sciatica, ectopic chondrogenesis, etc. would be involved or it is highly likely to suffer from these diseases in the future.

Also, the antibody of the present invention can be employed for detecting the polypeptide of the present invention, which may be present in a test sample fluid such as a body fluid, a tissue, etc. The antibody can also be used for preparation of an antibody column for purification of the polypeptide of the present invention, detection of the polypeptide of the present invention in the fractions upon purification, and analysis of the behavior of the polypeptide of the present invention in the cells under investigation.

(4) Gene Diagnostic Agent

By using the DNA of the present invention, e.g., as a probe, an abnormality (gene abnormality) of the DNA or mRNA encoding the polypeptide of the present invention in human or other warm-blooded animal (e.g., rat, mouse, guinea pig, rabbit, chicken, sheep, swine, bovine, horse, cat, dog, monkey, chimpanzee, etc.) can be detected. Therefore, the DNA of the present invention is useful as a gene diagnostic agent for the damage to the DNA or mRNA, its mutation, or its decreased expression, or increased expression or overexpression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

When the decreased expression is detected by, e.g., the Northern hybridization, it can be diagnosed that it is highly likely to suffer from diseases, e.g., chronic rheumatoid arthritis, arthrosis deformans, osteoporosis, bone fracture, cancer, etc.

On the other hand, when the overexpression is detected by the Northern hybridization, it can also be diagnosed that it is highly likely to suffer from diseases, e.g., intervertebral disk hernia, sciatica, ectopic chondrogenesis, etc.

When mutation of DNA was detected by PCR-SSCP, it can be diagnosed that it is highly likely to suffer from diseases, e.g., intervertebral disk hernia, sciatica, ectopic chondrogenesis, or chronic rheumatoid arthritis, arthrosis deformans, osteoporosis, bone fracture, cancer, etc (5) Pharmaceuticals Comprising Antisense DNA Antisense DNA that binds to the DNA of the present invention complementarily and inhibits the expression of the DNA can suppress the functions of the polypeptide of the present invention or the DNA of the present invention in vivo, and can be used as the agent for the treatment/prevention of diseases, e.g., intervertebral disk hernia, sciatica, ectopic chondrogenesis, etc.

In the case that the antisense DNA described above is used for the therapeutic/prophylactic agent described above, the antisense DNA can apply similarly to the therapeutic/prophylactic agent for various diseases, which contains the DNA of the present invention described above.

For example, when the antisense DNA is used, the antisense DNA alone is administered, or the antisense DNA is inserted into an appropriate vector such as retrovirus vector, adenovirus vector, adenovirus-associated virus vector, etc. followed by treating in a conventional manner. The antisense DNA may be administered as it stands, or may be prepared into the dosage form with a physiologically acceptable carrier to increase its uptake and administered by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(6) Pharmaceuticals Comprising the Antibody of the Present Invention

The antibody of the present invention which possesses the effect of neutralizing the activities of the polypeptide of the present invention can be used as drugs for the treatment/prevention of diseases, e.g., intervertebral disk hernia, sciatica, ectopic chondrogenesis, etc.

The therapeutic/prophylactic agent containing the antibody of the present invention described above may be administered orally or parenterally to human or mammal (e.g., rat, rabbit, sheep, swine, bovine, cat, dog, monkey, etc.) as a liquid preparation in its original form, or as a pharmaceutical composition in an appropriate drug form. The dose varies depending on subject to be administered, target disease, conditions, route for administration, etc.; for example, when used for the treatment/prevention of intervertebral disk hernia, the antibody of the present invention is intravenously administered to adult normally in a single dose of about 0.01 mg to about 20 mg/kg body weight, preferably about 1.0 to about 10 mg/kg body weight, and more preferably about 0.1 to about 5 mg per day once to about 5 times a day, preferably once to about 3 times. In parenteral administration in other route and in oral administration, a dose similar to those given above can be administered. Where conditions are serious, the dose may be increased depending on the conditions.

The antibody of the present invention may be administered in itself or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol, polyethylene glycol), nonionic surfactant [e.g., polysorbate 80™, HCO-50 (polyoxyethylene (50 mol) adduct of hydrogenated castor oil)] may be used in combination. For the oily solution, for example, sesame oil, soybean oil and the like are used, and dissolution aids such as benzyl benzoate and benzyl alcohol may be used in combination. The thus prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(7) DNA Transgenic Animal

The present invention provides a non-human mammal bearing the DNA encoding the polypeptide of the present invention, which is exogenous (hereinafter referred to as the exogenous DNA of the present invention) or its mutant DNA (sometimes simply referred to as the exogenous mutant DNA of the present invention).

Thus, the present invention provides:

(i) a non-human mammal bearing the exogenous DNA or its mutant DNA;

(ii) the mammal according to (i), wherein the non-human mammal is a rodent;

(iii) the mammal according to (ii), wherein the rodent is mouse or rat; and, (iv) a recombinant vector bearing the exogenous DNA of the present invention or its mutant DNA and capable of expressing in a mammal.

The non-human mammal bearing the exogenous DNA of the present invention or its mutant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goat, rabbits, dogs, cats, guinea pigs, hamsters, rats, mice and the like. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in mammals include, in addition to the aforesaid non-human mammals, human, etc.

The exogenous DNA of the present invention refers to the DNA of the present invention that is once isolated and extracted from mammals not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean the DNA that expresses the abnormal polypeptide of the present invention and exemplified by such a DNA that expresses a protein capable of suppressing the functions of the normal polypeptide of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include 1) promoters for DNA derived from viruses (e.g., simian virus, cytomegalovirus, Moloney leukemia virus, JC virus, breast cancer virus, poliovirus, etc.), and 2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin; etc. Among them, cytomegalovirus promoters, human polypeptide elongation factor 1α (EF-1α) promoters, human and chicken β actin promoters etc., which can highly express in the whole body are preferred.

It is preferred that the vectors described above have a sequence for terminating the transcription of the desired messenger RNA in the DNA transgenic animal (generally termed terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can be obtained using complementary DNA prepared by a publicly known method from RNA of human fibroblast origin as a starting material. Alternatively, the translational region for a normal polypeptide translational region obtained by the cell or tissue described above can be made variant by point mutagenesis.

The translational region can be prepared by a conventional DNA engineering technique in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention is expressed to a high level, and may eventually develop the hyperfunction of the polypeptide of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction by the polypeptide of the present invention and to clarify the pathological mechanism of the disease associated with the protein of the present invention and to determine how to treat the disease.

Furthermore, since a mammal transfected the exogenous normal DNA of the present invention exhibits an increasing symptom of the polypeptide librated, the animal is usable for screening of therapeutic agents agent for the disease associated with the polypeptide of the present invention.

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of the polypeptide of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of the polypeptide of the present invention and to study a method for treatment of this disease.

More specifically, the transgenic animal of the present invention expressing the abnormal DNA of the present invention to a high level is also expected to serve as an experimental model for the elucidation of the mechanism of the functional inhibition (dominant negative effect) of a normal polypeptide by the abnormal polypeptide of the present invention in the function in active type inadaptability of the polypeptide of the present invention.

A mammal bearing the abnormal exogenous DNA of the present invention is also expected to serve for screening a candidate drug for the treatment of the function inactive type inadaptability of the polypeptide of the present invention, since the polypeptide of the present invention is increased in such an animal in its free form.

Other potential applications of two kinds of the transgenic animals described above include:
1) use as a cell source for tissue culture;
2) elucidation of the association with a polypeptide that is specifically expressed or activated by the polypeptide of the present invention, through direct analysis of DNA or RNA in tissue of the DNA transgenic animal of the present invention or by analysis of the polypeptide tissue expressed by the DNA;
3) research in the function of cells derived from tissues that are cultured usually only with difficulty, using cells of tissue bearing the DNA cultured by a standard tissue culture technique;
4) screening for a drug that enhances the functions of cells using the cells described in 3) above; and,
5) isolation and purification of the variant polypeptide of the present invention and preparation of an antibody thereto.

Furthermore, clinical conditions of a disease associated with the polypeptide of the present invention, including the function inactive type inadaptability of the polypeptide of the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free DNA transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the polypeptide of the present invention, and as studies on association with apoptosis, differentiation or propagation or on the mechanism of signal transduction in these properties to inspect any abnormality therein. Thus the DNA transgenic animal of the present invention can provide an effective research material for the polypeptide of the present invention and for elucidating the function and effect thereof.

To develop pharmaceuticals for the treatment of diseases associated with the polypeptide of the present invention, including the function inactive type inadaptability of the polypeptide of the present invention, using the DNA transgenic animal of the present invention, an effective and rapid method for screening can be provided by using the method for inspection and the method for quantification, etc.

described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:
(i) a non-human embryonic stem cell in which the DNA of the present invention is inactivated;
(ii) the embryonic stem cell according to (i), wherein the DNA is inactivated by introducing a reporter gene (e.g., β-galactosidase gene derived from *Escherichia coli*);
(iii) the embryonic stem cell according to (i), which is resistant to neomycin;
(iv) the embryonic stem cell according to (i), wherein the non-human mammal is a rodent;
(v) an embryonic stem cell according to (iv), wherein the rodent is mouse;
(vi) a non-human mammal deficient in expressing the DNA of the present invention, wherein the DNA of the present invention is inactivated;
(vii) the non-human mammal according to (v), wherein the DNA is inactivated by inserting a reporter gene (e.g., β-galactosidase derived from *Escherichia coli*) therein and the reporter gene is capable of being expressed under control of a promoter for the DNA of the present invention;
(viii) the non-human mammal according to (vi), which is a rodent;
(ix) the non-human mammal according, to (viii), wherein the rodent is mouse; and,
(x) a method for screening a compound or its salt that promotes or inhibits the promoter activity for the DNA of the present invention, which comprises administering a test compound to the mammal of (vii) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention (hereinafter sometimes referred to as the knockout DNA of the present invention) by substantially inactivating the activities of the polypeptide of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons to, thus inhibit the synthesis of complete messenger RNA and eventually destroy the gene (hereinafter simply referred to as targeting vector). The thus obtained ES cells to the Southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is desirable to identify sexes as soon as possible also in order to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to spontaneously differentiate them to various cell types, for example, pariental and visceral muscles, cardiac muscle or the like (M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985). The cells deficient in expression of the DNA of the present invention, which are obtainable from the differentiated ES cells of the present invention, are useful for studying the functions of the polypeptide of the present invention cytologically or molecular biologically.

The non-human mammal deficient in expression of the DNA of the present invention can be identified from a normal animal by measuring the amount of mRNA in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The knockout cells with the DNA of the present invention disrupted can be identified by Southern hybridization analysis with a DNA fragment on or near the DNA of the present invention as a probe, or by PCR analysis using a DNA sequence on the targeting vector and another DNA sequence which is not included in the targeting vector as primers. When non-human mammalian embryonic stem cells are used, a cell line wherein the DNA of the present invention is inactivated by homologous recombination is cloned; the resulting cloned cell line is injected to, e.g., a non-human mammalian embryo or blastocyte, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the peptide of the present invention. The individuals deficient in homozygous expression of the polypeptide of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal in which the DNA of the present invention is inactivated lacks various biological activities derived from the polypeptide of the present invention, such an animal can be a disease model suspected of inactivated biological activities of the polypeptide of the present invention and thus, offers an effective study to investigate causes for and therapy for these diseases.

(8a) Method for Screening of Compounds Having Therapeutic/Prophylactic Effects for Diseases Caused by Deficiency, Damages, Etc. of the DNA of the Present Invention The non-human mammal deficient in expression of the DNA of the present invention can be employed for the screening of compounds having therapeutic/prophylactic effects for diseases (chronic rheumatoid arthritis, arthrosis deformans, osteoporosis, fracture, cancer, etc.) caused by deficiency, damages, etc. of the DNA of the present invention.

That is, the present invention provides a method for screening of a compound having therapeutic/prophylactic effects for diseases caused by deficiency, damages, etc. of the DNA of the present invention, which comprises administering a test compound to the non-human mammal deficient in expression of the DNA of the present invention and observing and measuring a change occurred in the animal.

As, the non-human mammal deficient in expression of the DNA of the present invention, which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma and the like and these compounds may be novel compounds or publicly known compounds.

Specifically, the non-human mammal deficient in the expression of the DNA of the present invention is treated with a test compound, comparison is made with an intact animal for control and a change in each organ, tissue, disease conditions, etc. of the animal is used as an index to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, an amount of a test compound administered can be selected depending on administration route, nature of the test compound, and the like.

For example, in the case of screening a compound having a therapeutic/prophylactic effect for diseases such as chronic rheumatoid arthritis, arthrosis deformans, osteoporosis, bone fracture, cancer, etc., the non-human mammal deficient in expression of the DNA of the present invention is subjected to a sugar loading treatment, a test compound is administered before or after the sugar loading treatment and, blood sugar level, body weight change, etc. of the animal is measured with passage of time.

In the screening method supra, when a test compound is given to an animal to be tested and found to reduce the blood sugar level of the animal to at least about 10%, preferably at least about 30% and more preferably at least about 50%, the test compound can be selected as a compound having the therapeutic and prophylactic effect for the diseases supra.

The compound obtained using the above screening method is a compound selected from the test compounds described above and exhibits a therapeutic/prophylactic effect for the diseases (chronic rheumatoid arthritis, arthrosis deformans, osteoporosis, bone fracture, cancer, etc.) caused by deficiencies, damages, etc. of the polypeptide of the present invention. Therefore, the compound can be employed as a safe and low toxic drug for the treatment and prevention of these diseases. Furthermore, compounds derived from such a compound obtained by the screening supra can be likewise employed.

The compound obtained by the screening above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical containing the compound obtained by the above screening method or salts thereof may be manufactured in a manner similar to the method for preparing the composition comprising the polypeptide of the present invention described hereinabove.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

Although the amount of the compound or its salt to be administered varies depending upon particular disease, subject to be administered, route of administration, etc., but when the compound is orally administered for the purpose of chronic rheumatoid arthritis, the compound is generally administered to an adult (as 60 kg body weight) in a dose of about 0.1 mg/day to about 100 mg/day, preferably about 1.0 mg/day to about 50 mg/day, more preferably about 1.0 mg to about 20 mg. For parenteral administration, a single dose of the compound varies depending upon subject to be administered, target disease, etc., but when the compound is administered to an adult (as 60 kg body weight) in the form of an injectable preparation for the purpose of chronic rheumatoid arthritis, it is generally advantageous to administer the compound intravenously in a dose of about 0.01 mg/day to about 30 mg/day, preferably about 0.1 mg/day to about 20 mg/day, more preferably about 0.1 mg/day to about 10 mg/day, though the single dosage varies depending upon particular subject, particular disease, etc. As for other animals, the composition can be administered in the above amount with converting it into that for the body weight of 60 kg.

(8b) Method for Screening a Compound that Promotes or Inhibits the Activities of a Promoter to the DNA of the Present Invention The present invention provides a method for screening a compound or its salt that promotes or inhibits the activities of a promoter to the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene can be expressed under control of a promoter to the DNA of the present invention.

The same examples of the test compound apply to specific compounds used for the screening.

As the reporter gene, the same specific examples described above apply, and β-galactosidase (lacZ), soluble alkaline phosphatase gene, luciferase gene and the like are preferably employed.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, instead of the polypeptide of the present invention. Thus, the state of expression of the polypeptide of the present invention can be readily observed in vivo of an animal by staining with a reagent, e.g., 5-bromo-4-chloro-3-indolyl-β-galactopyranoside (X-gal), which is substrate for β-galactosidase. Specifically, a mouse deficient in the polypeptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method supra are compounds that are selected from the test compounds described above and that promote or inhibit the promoter activity to the DNA of the present invention.

The compound obtained by the screening method above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that promote the promoter activity to the DNA of the present invention can promote the expression of the polypeptide of the present invention, or can promote the functions of the polypeptide, they are useful as safe and low toxic pharmaceuticals for the treatment/prevention of diseases such as chronic rheumatoid arthritis, arthrosis deformans, osteoporosis, bone fracture, cancer, etc.

On the other hand, the compounds or salts thereof that inhibit the promoter activity to the DNA of the present invention can inhibit the expression of the polypeptide of the present invention, or can inhibit the functions of the polypeptide, they are useful as safe and low toxic pharmaceuticals for the treatment/prevention of diseases such as intervertebral disk hernia, osphyalgia, ectopic chondrogenesis, etc.

In addition, compound derived from the compounds obtained by the screening above may be likewise employed.

A pharmaceutical containing the compounds or salts thereof obtained by the screening method supra may be manufactured in a manner similar to the method for preparing the pharmaceutical containing the polypeptide of the present invention described above.

Since the pharmaceutical preparation thus obtained is safe and low toxic, it can be administered to human or another mammal (e.g.; rat, mouse, guinea pig, rabbit, sheep, swine, bovine, horse, cat, dog, monkey, etc.).

The dose of the compound or salts thereof varies depending on target disease, subject to be administered, route for administration, etc.; for example, when the compound that promotes the promoter activity to the DNA of the present invention is orally administered for the purpose of treating chronic rheumatoid arthritis, the dose is normally about 0.1 to about 100 mg, preferably about 1.0 to about 50 mg, more preferably about 1.0 to about 20 mg per day for adult (as 60 kg body weight). In parenteral administration, a single dose of the compound varies depending on subject to be administered, target disease, etc. but when the compound that promotes the promoter activity to the DNA of the present invention is administered in the form of injectable preparation for the purpose of treating chronic rheumatoid arthritis, it is advantageous to administer the compound intravenously at a single dose of about 0.01 to about 30 mg/day, preferably about 0.1 to about 20 mg/day, more preferably about 0.1 to about 10 mg/day for adult (as 60 kg body weight). For other animal species, the corresponding dose as converted per 60 kg weight can be administered.

On the other hand, when the compound that inhibits the promoter activity to the DNA of the present invention is orally administered for the purpose of treating intervertebral disk hernia, the dose is normally about 0.1 to about 100 mg, preferably about 1.0 to about 50 mg, more preferably about 1.0 to about 20 mg per day for adult (as 60 kg body weight). In parenteral administration, a single dose of the compound varies depending on subject to be administered, target disease, etc. but when the compound that inhibits the promoter activity to the DNA of the present invention is administered in the form of injectable preparation for the purpose of treating intervertebral disk hernia, it is advantageous to administer the compound intravenously at a single dose of about 0.01 to about 30 mg/day, preferably about 0.1 to about 20 mg/day, more preferably about 0.1 to about 10 mg/day for adult (as 60 kg body weight). For other animal species, the corresponding dose as converted per 60 kg weight can be administered.

As stated above, the non-human mammal deficient in expression of the DNA of the present invention is extremely useful for screening the compound or its salt that promotes or inhibits the activity of a promoter to the DNA of the present invention and can greatly contribute to the elucidation of causes for various diseases suspected of deficiency in expression of the DNA of the present invention and for the development of prophylactic/therapeutic agent for these diseases.

Furthermore, a so-called transgenic animal (gene transferred animal) can be prepared by using DNA containing a promoter region of the protein of the present invention, ligating genes encoding various proteins downstream and injecting the same into oocyte of an animal. It is then possible to synthesize the protein therein specifically and study its activity in vivo. When an appropriate reporter gene is ligated to the promoter site above and a cell line that express the gene is established, the resulting system can be utilized as the survey system for a low molecular compound having the action of specifically promoting or inhibiting the in vivo productivity of the polypeptide per se of the present invention.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |

| | -continued |
|---|---|
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

Also, substituents, protecting groups, and reagents frequently used in this specification are presented as the codes below.

| | |
|---|---|
| Me | methyl group |
| Et | ethyl group |
| Bu | butyl group |
| Ph | phenyl group |
| TC | thiazolidine-4(R)-carboxamide group |
| Tos | p-toluenesulfonyl |
| CHO | formyl |
| Bzl | benzyl |
| Cl$_2$Bzl | 2,6-dichlorobenzyl |
| Bom | benzyloxymethyl |
| Z | benzyloxycarbonyl |
| Cl-Z | 2-chlorobenzyl oxycarbonyl |
| Br-Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

The sequence identification numbers in the sequence listing of the specification indicates the following sequence, respectively.

[SEQ ID NO:1]

This shows the base sequence of the synthetic DNA (upper strand) of the cis-element, used in EXAMPLE 1.

[SEQ ID NO:2]

This shows the base sequence of the synthetic DNA (lower strand) of the cis-element, used in EXAMPLE 1.

[SEQ ID NO:3]

This shows the base sequence of human-derived regulatory, transcription factor gene.

[SEQ ID NO:4]

This shows the amino acid sequence of human-derived regulatory transcription factor.

[SEQ ID NO:5]
This shows the amino acid sequence of C-terminal 90 amino acid residues of human-derived regulatory transcription factor.

[SEQ ID NO:6]
This shows the base sequence of mouse-derived regulatory transcription factor gene.

[SEQ ID NO:7]
This shows the amino acid sequence of mouse-derived regulatory transcription factor.

[SEQ ID NO:8]
This shows the base sequence of the primer used in EXAMPLE 2.

[SEQ ID NO:9]
This shows the base sequence of the primer used in EXAMPLE 2.

[SEQ ID NO:10]
This shows the base sequence of the primer used in EXAMPLE 2.

[SEQ ID NO:11]
This shows the base sequence of the primer used in EXAMPLE 2.

[SEQ ID NO:12]
This shows the base sequence of the primer used, in EXAMPLE 3.

[SEQ ID NO:13]
This shows the base sequence of the primer used in EXAMPLE 3.

[SEQ ID NO:14]
This shows the base sequence of human ChM-I promoter.

[SEQ ID NO:15]
This shows the base sequence of the primer used in EXAMPLE 1.

[SEQ ID NO:16]
This shows the base sequence of the primer used in EXAMPLE 1.

[SEQ ID NO:17]
This shows the cis-element of human ChM-I gene promoter.

[SEQ ID NO:18]
This shows the base sequence of the DNA encoding the polypeptide having the amino acid sequence represented by SEQ ID NO:5.

[SEQ ID NO:19]
This shows the amino acid sequence of the C-terminal 90 amino acid residue of mouse-derived regulatory transcription factor.

[SEQ ID NO:20]
This shows the base sequence of the DNA encoding the polypeptide having the amino acid sequence represented by SEQ ID NO:19.

[SEQ ID NO:21]
This shows the cis-element of human ChM-I gene promoter.

[SEQ ID NO:22]
This shows the base sequence of the primer used in EXAMPLE 4.

[SEQ ID NO:23]
This shows the base sequence of the primer used in EXAMPLE 4.

[SEQ ID NO:24]
This shows the base sequence of the primer used in EXAMPLE 5.

[SEQ ID NO:25]
This shows the base sequence of the primer used in EXAMPLE 5.

[SEQ ID NO:26]
This shows the base sequence of the primer used in EXAMPLE 6.

[SEQ ID NO:27]
This shows the base sequence of the primer used in EXAMPLE 6.

*Escherichia coli* TOP10/pTB2074 bearing vector pTB2074 obtained in EXAMPLE 2 later described was on deposit with the Ministry of International Trade and Industry, Agency of Industrial Science and Technology, National Institute of Bioscience and Human Technology (NIBH) located at 1-1-3, Higashi, Tsukuba-shi, Ibaraki, Japan, as the Accession Number FERM BP-6886 on Sep. 22, 1999 and with Institute for Fermentation, Osaka (IFO) located at 2-17-85, Juso Honcho, Yodogawa-ku, Osaka-shi, Osaka, Japan, as the Accession Number IFO 16299 on Jul. 21, 1999.

*Escherichia coli* JM109/pTB2075 bearing plasmid pTB2075 obtained in EXAMPLE 1 later described was on deposit with the Ministry of International Trade and Industry, Agency of Industrial Science and Technology, National Institute of Bioscience and Human Technology (NIBH) located at 1-1-3, Higashi, Tsukuba-shi, Ibaraki, Japan, as the Accession Number FERM BP-6887, on Sep. 22, 1999 and with Institute for Fermentation, Osaka (IFO) located at 2-17-85, Juso Honcho, Yodogawa-ku, Osaka-shi, Osaka, Japan, as the Accession Number IFO 16300 on Jul. 21, 1999.

Hereinafter the present invention is specifically described below with reference to EXAMPLES, but not intended to limit the scope of the present invention thereto. The gene manipulation procedures using *Escherichia coli* were performed according to the methods described in the Molecular Cloning.

EXAMPLE 1

Cloning of Human Cartilage-Derived Regulatory Transcription Factor Gene Binding to Human ChM-I Gene Promoter Using primers (SEQ ID NO:15 and SEQ ID NO:16) designed based on the human ChM-I genome gene sequence described in Japanese Patent Laid-Open Application No. 7-138295 and Human Genome Walker kit (Clontech), human ChM-I promoter was acquired in accordance with the procedures described in the kit. A part of the base sequence was determined (SEQ ID NO:16) and as a result, the base sequence was different in one base from the sequence described in Japanese Patent Laid-Open Application No. 7-138295. DNA of the base sequence: GCTGGAAGGGGTGGGGACCG (SEQ ID NO:17) containing this different base was selected as the cis-element. Hereinafter, the experiment was carried out in accordance with the user's manual and handbook attached to Matchmaker one-hybrid system (Clontech, Inc.), unless otherwise indicated.

A DNA having the base sequence (SEQ ID NO:1) containing 3 repetitions of the base sequence shown by GCTGGAAGGGGTGGGGACCG (SEQ ID NO:17) and a DNA containing the complementary sequence (SEQ ID NO:2) to the sequence shown by SEQ ID NO:1 were synthesized and annealed. The double stranded DNA obtained was inserted into EcoRI-XbaI site of plasmid pHISi attached to Matchmaker one-hybrid system (Clontech, Inc.) to produce reporter plasmid pHISi-56 for the yeast one-hybrid method. pHISi-56 was transfected to yeast (Saccharomyces Cerevisiae) YM4271 strain attached to Matchmaker one hybrid system (Clontech, Inc.) to obtain His3$^+$ transformant (YM4271::pHISi-56). However, proliferation of YM4271::pHISi-56 was not completely suppressed even in the presence of 60 mM 3-aminotriazole.

Consequently, improvement was made on the reporter plasmid to construct pTB2075 (FIG. 2). pTB2075 is inserted (1) with EcoRI-BamHI fragment (1.4 kb fragment containing the GCTGGMGGGGTGGGGACCG (SEQ ID NO: 17) sequence repeated thrice and the HIS3 gene) of pHISi-56 into the EcoRI-BamHI site of pBR22, and (2) with SphI-PvuII fragment (1.0 kb fragment containing TRP1 gene) derived from blunted pBD-GAL4 Cam (Stratagene, Inc.) into the blunted SphI-PvuII site of pBR322, respectively.

Plasmid pTB2075 was cleaved with XhoI followed by transfection to yeast YM4271 strain. Thus, the transformant of Trp1$^+$ (YM4271::pTB2075) was obtained. Human chondrocyte matchmaker cDNA library (Clontech, Inc.) was introduced into YM4271::pTB2075, and yeast showing phenotype of His$^+$ and Leu$^+$ was selected. After plasmid DNA was recovered from the yeast, the recovered plasmid DNA was again transfected to YM4271::pTB2075, whereby the phenotype of His$^+$ and Leu$^+$ could be confirmed in 4 clones. The base sequence of plasmid DNA in each clone was determined. As a result, it was revealed that they were derived from one gene, though they were different in length of the inserted fragments. In these DNAs, the base sequence of the longest DNA was that represented by SEQ ID NO:3 and the amino acid sequence of the protein encoded by the DNA was the one represented by SEQ ID NO:4 (FIG. 3). The DNA represented by SEQ ID NO:3 was a partial gene lacking the gene portion encoding the N-terminal region.

In the plasmid DNAs of the 4 clones obtained, YM4271::pTB2075 was transfected with plasmid (pHT56-H6) inserted with the shortest DNA (SEQ ID NO:18) to optionally select 10 transformants showing phenotype of Leu$^+$. These transformants all showed the phenotype of His3$^+$.

Based on the foregoing, it was revealed that the protein having the amino acid sequence represented by SEQ ID NO:4 bound to the DNA having the base sequence represented by GCTGGAAGGGGTGGGGACCG (SEQ ID NO:17), which was the cis-element used; it was also revealed that the C-terminal 90 amino acids (SEQ ID NO:5) may constitute the region necessary for the binding.

Based on the foregoing, inhibitors of regulatory transcription factors, etc. can be surveyed by selecting compounds showing no growth inhibition (anti-fungal action) in a medium supplemented with histidine and showing growth inhibition in a histidine-free medium, using pHT56-H6-transfected yeast YM4271::pTB2075 strain.

EXAMPLE 2

Acquisition of Mouse-Derived Full-Length cDNA and Construction of Animal Cell Expression Vector.

Two primers (SEQ ID NO:8 and SEQ ID NO:9) were designed based on SEQ ID NO:4. Using these primers, PCR was performed on Fetal Mouse Library Master DNA Plate (OriGene Technologies, Inc., Lot #004) according to the protocol. The results reveal that mouse homologue of the regulatory transcription factor gene obtained in EXAMPLE 1 was contained in the well 4F. Following the protocol, subplate (Fetal mouse library plate 4F Lot #001) was obtained to confirm the presence of mouse-derived regulatory transcription factor gene in the well 7A of the subplate. Sequencing of the DNA contained in the well 7A was made according to the 5'-RACE method and the 3'-RACE method, respectively. As a result, it was found that mouth-derived full-length regulatory transcription factor gene was contained in the well 7A.

Based on the sequence information obtained, two primers (SEQ ID NO:10 and SEQ ID NO:11) were designed. PCR was performed to the well 7A of the subplate and the resulting amplified fragment was cloned to pCRII (Invitrogen). Determination of its base sequence revealed that the DNA having the base sequence represented by SEQ ID NO:6 encoded a protein (SEQ ID NO:7) composed of 508 amino acid residues (FIG. 4). Comparison of a partial protein of human-derived regulatory transcription factor having the amino acid sequence represented by SEQ ID NO:7 to the amino acid sequence of mouse-derived regulatory transcription factor having the amino acid sequence represented by SEQ ID NO:4 indicated 88% homology.

Next, plasmid having the base sequence encoding the protein composed of 508 amino acid residues was digested with restriction enzymes HindIII and NotI. The resulting fragment of about 2300 bp was ligated to pcDNA3.1(+) (Invitrogen) that was similarly digested with the restriction enzymes. Vector pTB2074, in which the protein-encoding region of this gene was ligated at the downstream of CMV promoter of pcDNA3.1(+), was acquired for expression of animal cells.

EXAMPLE 3

Detection of mRNA in the Gene by PCR

Chondromodulin-I (ChM-I) is expressed by culturing mouse ATDC5 cells in the presence of insulin (Int. J. Dev. Biol., 43:39, 1999). According to this report, ATDC5 cells were cultured and cells were recovered within the period ChM-I was supposed to be expressed. The total RNA was extracted using RNeasy (Qiagen). Next, after DNaseI treatment using Message Clean Kit (GenHunter), this RNA was subjected to reverse transcription in accordance with the protocol of RNA PCR Kit (Takara Shuzo Co., Ltd.) to acquire cDNA. PCR was performed using this cDNA as a template. When two primers (SEQ ID NO:12 and SEQ ID NO:13) designed based on cDNA sequence of mouse ChM-I (Int. J. Dev. Biol., 43:39, 1999, Genbank accession number U43509) were used, the band (201 bp) from ChM-I gene was detected by agarose gel electrophoresis. Similarly when a primer having the base sequence represented by SEQ ID NO:8 and a primer having the base sequence represented by SEQ ID NO:9 were used, expression (567 bp) of the gene having the base sequence represented by SEQ ID NO:6 was detected. It was thus confirmed that the two were expressed within the same period.

Using Mouse Multiple Tissue cDNA Panel I (CLONTECH), further analysis was conducted with respect to organs, in which the gene having the base sequence represented by SEQ ID NO:6 were expressed. Using the primer having the base sequence represented by SEQ ID NO:8 and the primer having the base sequence represented by SEQ ID NO:9, PCR (28 cycles) was carried out in accordance with the protocol attached. Strong expression of mRNA was noted in the liver and the heart, and second strong expression of mRNA was noted in the skeletal muscle and on days 11, 15 and 17 of the fetus.

As such, the use of primers designed based on the DNA sequence of regulatory transcription factor gene enables to detect expression (mRNA) of the regulatory transcription factor gene, which can be utilized to search pharmaceuticals such as expression promoters or expression inhibitors of the regulatory transcription factor gene.

EXAMPLE 4

Effect of Mouse Fibloblast Cell Line C3H/10T1/2 on Cartilage Differentiation by pTB2074 Transfection Mouse fibloblast cell line C3H/10T1/2, Clone 8 (ATCC Accession No. CCL-226) was cultured in DMEM (GIBCO) containing 10% FBS. About 150,000 cells/well was seeded on a 24-well plate. On the following day, a mixture of pTB2074 or pcDNA3.1 (+) (Invitrogen) obtained in EXAMPLE 2 and Fugene6 (Boehringer) was added to the cells for transfection. On day 2 after the transfection, RNA was extracted using RNeasy Mini Kit (Qiagen) and then subjected to DNase processing using Message Clean Kit (GenHunter), which was used as RNA sample.

Using this RNA sample as a template, primers (SEQ ID NO:22 and SEQ ID NO:23) were prepared based on the sequence of mouse Type II B collagen gene (Col2a1). Using the primers and RT-PCR kit (Takara Shuzo Co., Ltd.), RT-PCR was performed. After agarose gel electrophoresis, comparison was made on the objective bands using Gel Image (Genomic Solutions).

The results showed that expression of Col2a1, which was a cartilage differentiation marker when pTB2074 was transfected to C3H/10T1/2, Clone 8 cell line, was increased to about 2.5 times, as compared to the case when pcDNA3.1(+) was transfected to C3H/10T1/2, Clone 8 cell line.

EXAMPLE 5

Effect of Human Dedifferentiated Chondrocyte on Cartilage Differentiation by pTB2074 Transfection Human normal chondrocytes (purchased from Toyobo) were cultured on a cell culture dish (Falcon) using Chondrocytes growth medium supplied with the human normal chondrocyte culture kit. The chondrocytes were dedifferentiated due to dish culturing on a dish, resulting in failure to express chondrocyte marker Type II collagen gene (dedifferentiated chondrocytes). The chondrocytes were seeded on a 24-well plate in about 150,000 cells/well. On the following day, transfection was effected by adding a mixture of vector pTB2074 or pcDNA3.1(+) (Invitrogen) obtained in EXAMPLE 2 and Fugene6 (Boehringer). After RNA sample was obtained in a manner similar to the procedure described in EXAMPLE 4, RT-PCR was performed using the primers (SEQ ID NO:24 and SEQ ID NO:25) designed based on human Type II collagen gene (COL2A1).

The results showed that when pcDNA3.1(+) was transfected to human normal chondrocytes, expression of COL2A1 was not noted at all, whereas expression of COL2A1 was observed when pTB2074 was transfected to human normal chondrocytes.

EXAMPLE 6

Effect of Rabbit Chondrocytes on Cartilage Matrix Production by pTB2074 Transfection Joint cartilage collected from rabbit (Japanese white rabbit, male, 30 days old) was finely grounded, washed twice with 0.1% EDTA for 20 minutes and once with 1.25% trypsin for 60 minutes. The cartilage matrix was digested with 0.2% collagenase to recover joint chondrocytes. The chondrocytes were seeded on a 24-well collagen-coated plate (Falcon) in about 100,000 cells/wells, followed by culturing in α-MEM (GIBCO) containing 10% FBS for 5 days. Subsequently, the medium was exchanged. On the following day, transfection was effected by adding a mixture of vector pTB2074 or pcDNA3.1(+) (Invitrogen) obtained in EXAMPLE 2 and Fugene6 (Boehringer). After RNA sample was obtained in a manner similar to the procedure described in EXAMPLE 4, RT-PCR was performed using the primers (SEQ ID NO:26 and SEQ ID NO:27) designed based on rabbit Type II collagen gene (Biochimica et Biophysica Acta, vol. 1350, pp. 253-258 (1997); Col2a1).

The results showed that when pTB2074 was transfected to the rabbit chondrocytes described above, expression of Col2a1 increased approximately to twice, as compared to the case in which pcDNA3.1(+) was transfected to the rabbit chondrocytes described above.

Also, 10 ng/ml of IL-1β (Genzymetech) was added during the medium exchange described above, the transfection and acquisition of RNA sample were performed in a manner similar to the procedures described above, and expression of rabbit Type II collagen gene (Col2a1) was compared using RT-PCR.

The results showed that when pcDNA3.1(+) was transfected to the rabbit chondrocytes described above, expression of Col2a1 was not noted at all, whereas expression of Col2a1 was noted when pTB2074 was transfected to the rabbit chondrocytes described above.

INDUSTRIAL APPLICABILITY

The polypeptide of the present invention possesses the activity of binding specifically to the cis-element of ChM-I gene promoter to promote transcription of the ChM-I gene. Thus, the polypeptide of the present invention or the DNA of the present invention is useful as prophylactic/therapeutic agents for diseases, e.g., chronic rheumatoid arthritis, arthrosis deformans, osteoporosis, bone fracture, cancer, etc.

Also, the polypeptide of the present invention, the DNA of the present invention or the transformant of the present invention can be used for screening of compounds or salts thereof that promote or inhibit the activities of the polypeptide of the present invention The compounds or salts thereof that promote the activities of the polypeptide of the present invention or the expression of the DNA of the present invention are useful as prophylactic/therapeutic agents for diseases, e.g., chronic rheumatoid arthritis, arthrosis deformans, osteoporosis, bone fracture, cancer, etc. The compounds or salts thereof that inhibit the activities of the polypeptide of the present invention or the expression of the DNA of the present invention are useful as prophylactic/therapeutic agents for diseases, e.g., intervertebral disk hernia, sciatica, ectopic chondrogenesis, etc.

The antibody of the present invention can be used for quantitative assay for the polypeptide of the present invention and can be used as diagnostics for diseases associated with the polypeptide of the present invention.

The invention claimed is:

1. An isolated polypeptide or salt thereof, which polypeptide consists of the amino acid sequence of SEQ ID NO: 5.

2. An isolated polypeptide or salt thereof, which polypeptide consists of the amino acid sequence of SEQ ID NO: 4.

3. An isolated polypeptide or salt thereof, which polypeptide consists of the amino acid sequence of SEQ ID NO: 19.

4. An isolated polypeptide or salt thereof, which polypeptide consists of the amino acid sequence of SEQ ID NO: 7.

5. A kit for screening a compound or a salt thereof that promotes or inhibits the activity of the polypeptide or salt thereof according to any one of claims 1 to 4, comprising the polypeptide or salt thereof according to any one of claims 1 to 4.

6. A method of manufacturing the polypeptide or a salt thereof according to any one of claims 1 to 4, which comprises culturing a transformant transformed with a recombinant vector comprising a DNA comprising a base sequence encoding the polypeptide according to any one of claims 1 to 4 to produce the polypeptide or salt thereof according to any one of claims 1 to 4.

7. A method of screening a compound or a salt thereof that promotes or inhibits the activity of the polypeptide or salt thereof according to any one of claims 1 to 4, which comprises the steps of (i) contacting a DNA comprising a chondromodulin-I promoter with the polypeptide of any one of claims 1 to 4 in the presence and absence of a test compound, and (ii) comparing the amounts of the polypeptide bound to the chondromodulin-I promoter in the presence and absence of the test compound, thereby identifying the compound or salt thereof that promotes or inhibits the activity of the polypeptide or salt thereof of any one of claims 1 to 4 to the chondromodulin-I promoter.

* * * * *

UNITED STATES PATENT AND TRADEMARK OFFICE
CERTIFICATE OF CORRECTION

| | |
|---|---|
| PATENT NO. | : 7,241,860 B2 |
| APPLICATION NO. | : 10/130872 |
| DATED | : July 10, 2007 |
| INVENTOR(S) | : Yoshimura et al. |

Page 1 of 1

It is certified that error appears in the above-identified patent and that said Letters Patent is hereby corrected as shown below:

On the Cover page, first column, please insert the following foreign application priority data below the data set forth in field (87); insert:

Foreign Application Priority Data

November 26, 1999 ……………………. Japan 11/336475

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,241,860 B1 Page 1 of 1
APPLICATION NO. : 10/130872
DATED : July 10, 2007
INVENTOR(S) : Yoshimura et al.

It is certified that error appears in the above-identified patent and that said Letters Patent is hereby corrected as shown below:

On the Cover page, first column, please insert the following foreign application priority data below the data set forth in item (87):

Foreign Application Priority Data

November 26, 1999 ……………………….. Japan 11/336475

Signed and Sealed this

Eleventh Day of March, 2008

JON W. DUDAS
*Director of the United States Patent and Trademark Office*

SEQUENCE LISTING

<160> NUMBER OF SEQ ID NOS: 29

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic
      human chondromodulin-I gene cis-element. Upper strand.

<400> SEQUENCE: 1
aattcgctgg aaggggtggg gaccggctgg aagggtggg gaccggctgg aaggggtggg      60
gaccgt                                                                66

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: Synthetic
      human chondromodulin-I gene cis-element. Lower strand.

<400> SEQUENCE: 2
ctagacggtc cccaccccctt ccagccggtc cccacccctt ccagccggtc cccacccctt     60
ccagcg                                                                66

<210> SEQ ID NO 3
<211> LENGTH: 1669
<212> TYPE: DNA
<213> ORGANISM: Homo sapiens
<220> FEATURE:
<221> NAME/KEY: CDS
<222> LOCATION: (1)..(1212)

<400> SEQUENCE: 3

| | | | | | | | | | | | | | | | |
|---|---|---|---|---|---|---|---|---|---|---|---|---|---|---|---|
| gac | cag | aag | ctg | cag | gtc | tgc | tgc | agg | gtg | gag | gag | gtg | tgg | ctg | gca | 48 |
| Asp | Gln | Lys | Leu | Gln | Val | Cys | Cys | Arg | Val | Glu | Glu | Val | Trp | Leu | Ala | |
| 1 | | | | 5 | | | | | 10 | | | | | 15 | | |

| aaa | ctg | cag | ggc | ccc | tgt | ccc | cag | gca | cca | ccc | ctg | gag | ccc | gga | gcc | 96 |
|---|---|---|---|---|---|---|---|---|---|---|---|---|---|---|---|---|
| Lys | Leu | Gln | Gly | Pro | Cys | Pro | Gln | Ala | Pro | Pro | Leu | Glu | Pro | Gly | Ala | |
| | | 20 | | | | | 25 | | | | | 30 | | | | |

| cag | gcc | ctg | gcc | tac | agg | ccc | gtc | tcc | agg | aac | atc | gat | gtc | cca | aag | 144 |
|---|---|---|---|---|---|---|---|---|---|---|---|---|---|---|---|---|
| Gln | Ala | Leu | Ala | Tyr | Arg | Pro | Val | Ser | Arg | Asn | Ile | Asp | Val | Pro | Lys | |
| | 35 | | | | | 40 | | | | | 45 | | | | | |

| agg | aag | tcg | gac | gca | gtg | gaa | atg | gat | gag | atg | atg | gcg | gcc | atg | gtg | 192 |
|---|---|---|---|---|---|---|---|---|---|---|---|---|---|---|---|---|
| Arg | Lys | Ser | Asp | Ala | Val | Glu | Met | Asp | Glu | Met | Met | Ala | Ala | Met | Val | |
| 50 | | | | | 55 | | | | | 60 | | | | | | |

| ctg | acg | tcc | ctg | tcc | tgc | agc | cct | gtt | gta | cag | agt | cct | ccc | ggg | acc | 240 |
|---|---|---|---|---|---|---|---|---|---|---|---|---|---|---|---|---|
| Leu | Thr | Ser | Leu | Ser | Cys | Ser | Pro | Val | Val | Gln | Ser | Pro | Pro | Gly | Thr | |
| 65 | | | | 70 | | | | | 75 | | | | | 80 | | |

| gag | gcc | aac | ttc | tct | gct | tcc | cgt | gcg | gcc | tgc | gac | cca | tgg | aag | gag | 288 |
|---|---|---|---|---|---|---|---|---|---|---|---|---|---|---|---|---|
| Glu | Ala | Asn | Phe | Ser | Ala | Ser | Arg | Ala | Ala | Cys | Asp | Pro | Trp | Lys | Glu | |
| | | | | 85 | | | | | 90 | | | | | 95 | | |

| agt | ggt | gac | atc | tcg | gac | agc | ggc | agc | agc | act | acc | agc | ggt | cac | tgg | 336 |
|---|---|---|---|---|---|---|---|---|---|---|---|---|---|---|---|---|
| Ser | Gly | Asp | Ile | Ser | Asp | Ser | Gly | Ser | Ser | Thr | Thr | Ser | Gly | His | Trp | |
| | | | 100 | | | | | 105 | | | | | 110 | | | |

| agt | ggg | agc | agt | ggt | gtc | tcc | acc | ccc | tcg | ccc | cac | ccc | cag | gcc | | 384 |
|---|---|---|---|---|---|---|---|---|---|---|---|---|---|---|---|---|
| Ser | Gly | Ser | Ser | Gly | Val | Ser | Thr | Pro | Ser | Pro | His | Pro | Gln | Ala | | |
| | 115 | | | | | 120 | | | | | 125 | | | | | |

| agc | ccc | aag | tat | ttg | ggg | gat | gct | ttt | ggt | tct | ccc | caa | act | gat | cat | 432 |
|---|---|---|---|---|---|---|---|---|---|---|---|---|---|---|---|---|
| Ser | Pro | Lys | Tyr | Leu | Gly | Asp | Ala | Phe | Gly | Ser | Pro | Gln | Thr | Asp | His | |

-continued

```
              130                 135                 140
ggc ttt gag acc gat cct gac cct ttc ctg ctg gac gaa cca gct cca        480
Gly Phe Glu Thr Asp Pro Asp Pro Phe Leu Leu Asp Glu Pro Ala Pro
145                 150                 155                 160 cga aaa aga aag aac tct gtg aag gtg atg tac aag tgc ctg tgg cca        528
Arg Lys Arg Lys Asn Ser Val Lys Val Met Tyr Lys Cys Leu Trp Pro
                165                 170                 175 aac tgt ggc aaa gtt ctg cgc tcc att gtg ggc atc aaa cga cac gtc        576
Asn Cys Gly Lys Val Leu Arg Ser Ile Val Gly Ile Lys Arg His Val
            180                 185                 190 aaa gcc ctc cat ctg ggg gac aca gtg gac tct gat cag ttc aag cgg        624
Lys Ala Leu His Leu Gly Asp Thr Val Asp Ser Asp Gln Phe Lys Arg
        195                 200                 205 gag gag gat ttc tac tac aca gag gtg cag ctg aag gag gaa tct gct        672
Glu Glu Asp Phe Tyr Tyr Thr Glu Val Gln Leu Lys Glu Glu Ser Ala
    210                 215                 220 gct gct gct gct gct gct gcc gca ggc acc cca gtc cct ggg act ccc        720
Ala Ala Ala Ala Ala Ala Ala Gly Thr Pro Val Pro Gly Thr Pro
225                 230                 235                 240 acc tcc gag cca gct ccc acc ccc agc atg act ggc ctg cct ctg tct        768
Thr Ser Glu Pro Ala Pro Thr Pro Ser Met Thr Gly Leu Pro Leu Ser
                245                 250                 255 gct ctt cca cca cct ctg cac aaa gcc cag tcc tcc ggc cca gaa cat        816
Ala Leu Pro Pro Pro Leu His Lys Ala Gln Ser Ser Gly Pro Glu His
            260                 265                 270 cct ggc ccg gag tcc tcc ctg ccc tca ggg gct ctc agc aag tca gct        864
Pro Gly Pro Glu Ser Ser Leu Pro Ser Gly Ala Leu Ser Lys Ser Ala
        275                 280                 285 cct ggg tcc ttc tgg cac att cag gca gat cat gca tac cag gct ctg        912
Pro Gly Ser Phe Trp His Ile Gln Ala Asp His Ala Tyr Gln Ala Leu
    290                 295                 300 cca tcc ttc cag atc cca gtc tca cca cac atc tac acc agt gtc agc        960
Pro Ser Phe Gln Ile Pro Val Ser Pro His Ile Tyr Thr Ser Val Ser
305                 310                 315                 320 tgg gct gct gcc ccc tcc gcc gcc tgc tct ctc tct ccg gtc cgg agc       1008
Trp Ala Ala Ala Pro Ser Ala Ala Cys Ser Leu Ser Pro Val Arg Ser
                325                 330                 335 cgg tcg cta agc ttc agc gag ccc cag cag cca gca cct gcg atg aaa       1056
Arg Ser Leu Ser Phe Ser Glu Pro Gln Gln Pro Ala Pro Ala Met Lys
            340                 345                 350 tct cat ctg atc gtc act tct cca ccc cgg gcc cag agt ggt gcc agg       1104
Ser His Leu Ile Val Thr Ser Pro Pro Arg Ala Gln Ser Gly Ala Arg
        355                 360                 365 aaa gcc cga ggg gag gct aag aag tgc cgc aag gtg tat ggc atc gag       1152
Lys Ala Arg Gly Glu Ala Lys Lys Cys Arg Lys Val Tyr Gly Ile Glu
    370                 375                 380 cac cgg gac cag tgg tgc acg gcc tgc cgg tgg aag aag gcc tgc cag       1200
His Arg Asp Gln Trp Cys Thr Ala Cys Arg Trp Lys Lys Ala Cys Gln
385                 390                 395                 400 cgc ttt ctg gac tgagctgtgc tgcaggttct actctgttcc tggccctgcc          1252
Arg Phe Leu Asp ggcagccact gacaagaggc cagtgtgtca ccagccctca gcagaaaccg aaagagaaag    1312
aacggaaaca cggagtttgg gctctgttgg ctaaggtgta acacttaaag caattttctc    1372
ccattgtgcg aacattttat tttttaaaaa aaagaaacaa aaatattttt cccccctaaaa   1432 taggagagag ccaaaactga ccaaggctat tcagcagtga accagtgacc aaagaattaa    1492
ttaccctccg tttcccacat ccccactctc taggggatta gcttgtgcgt gtcaaaagaa    1552
```

```
ggaacagctc gttctgcttc ctgctgagtc ggtgaattct ttgctttcta aactcttcca    1612
gaaaggactg tgagcaagat gaatttactt ttcttaaaaa aaaaaaaaaa aaaaaaa       1669
```

<210> SEQ ID NO 4
<211> LENGTH: 404
<212> TYPE: PRT
<213> ORGANISM: Homo sapiens

<400> SEQUENCE: 4

```
Asp Gln Lys Leu Gln Val Cys Cys Arg Val Glu Val Trp Leu Ala
 1               5                  10                  15

Lys Leu Gln Gly Pro Cys Pro Gln Ala Pro Pro Leu Glu Pro Gly Ala
                20                  25                  30

Gln Ala Leu Ala Tyr Arg Pro Val Ser Arg Asn Ile Asp Val Pro Lys
            35                  40                  45

Arg Lys Ser Asp Ala Val Glu Met Asp Glu Met Met Ala Ala Met Val
        50                  55                  60

Leu Thr Ser Leu Ser Cys Ser Pro Val Val Gln Ser Pro Pro Gly Thr
65                  70                  75                  80

Glu Ala Asn Phe Ser Ala Ser Arg Ala Ala Cys Asp Pro Trp Lys Glu
                85                  90                  95

Ser Gly Asp Ile Ser Asp Ser Gly Ser Ser Thr Thr Ser Gly His Trp
            100                 105                 110

Ser Gly Ser Ser Gly Val Ser Thr Pro Ser Pro Pro His Pro Gln Ala
        115                 120                 125

Ser Pro Lys Tyr Leu Gly Asp Ala Phe Gly Ser Pro Gln Thr Asp His
    130                 135                 140

Gly Phe Glu Thr Asp Pro Asp Pro Phe Leu Leu Asp Glu Pro Ala Pro
145                 150                 155                 160

Arg Lys Arg Lys Asn Ser Val Lys Val Met Tyr Lys Cys Leu Trp Pro
                165                 170                 175

Asn Cys Gly Lys Val Leu Arg Ser Ile Val Gly Ile Lys Arg His Val
            180                 185                 190

Lys Ala Leu His Leu Gly Asp Thr Val Asp Ser Asp Gln Phe Lys Arg
        195                 200                 205

Glu Glu Asp Phe Tyr Tyr Thr Glu Val Gln Leu Lys Glu Glu Ser Ala
    210                 215                 220

Ala Ala Ala Ala Ala Ala Ala Gly Thr Pro Val Pro Gly Thr Pro
225                 230                 235                 240

Thr Ser Glu Pro Ala Pro Thr Pro Ser Met Thr Gly Leu Pro Leu Ser
                245                 250                 255

Ala Leu Pro Pro Leu His Lys Ala Gln Ser Ser Gly Pro Glu His
            260                 265                 270

Pro Gly Pro Glu Ser Ser Leu Pro Ser Gly Ala Leu Ser Lys Ser Ala
        275                 280                 285

Pro Gly Ser Phe Trp His Ile Gln Ala Asp His Ala Tyr Gln Ala Leu
    290                 295                 300

Pro Ser Phe Gln Ile Pro Val Ser Pro His Ile Tyr Thr Ser Val Ser
305                 310                 315                 320

Trp Ala Ala Ala Pro Ser Ala Ala Cys Ser Leu Ser Pro Val Arg Ser
                325                 330                 335

Arg Ser Leu Ser Phe Ser Glu Pro Gln Gln Pro Ala Pro Ala Met Lys
            340                 345                 350

Ser His Leu Ile Val Thr Ser Pro Pro Arg Ala Gln Ser Gly Ala Arg
```

```
                    355                 360                 365
Lys Ala Arg Gly Glu Ala Lys Lys Cys Arg Lys Val Tyr Gly Ile Glu
                370                 375                 380

His Arg Asp Gln Trp Cys Thr Ala Cys Arg Trp Lys Lys Ala Cys Gln
385                 390                 395                 400

Arg Phe Leu Asp

<210> SEQ ID NO 5
<211> LENGTH: 90
<212> TYPE: PRT
<213> ORGANISM: Homo sapiens

<400> SEQUENCE: 5

Ile Tyr Thr Ser Val Ser Trp Ala Ala Ala Pro Ser Ala Ala Cys Ser
  1               5                  10                  15

Leu Ser Pro Val Arg Ser Arg Ser Leu Ser Phe Ser Glu Pro Gln Gln
                 20                  25                  30

Pro Ala Pro Ala Met Lys Ser His Leu Ile Val Thr Ser Pro Pro Arg
             35                  40                  45

Ala Gln Ser Gly Ala Arg Lys Ala Arg Gly Glu Ala Lys Lys Cys Arg
         50                  55                  60

Lys Val Tyr Gly Ile Glu His Arg Asp Gln Trp Cys Thr Ala Cys Arg
 65                  70                  75                  80

Trp Lys Lys Ala Cys Gln Arg Phe Leu Asp
                 85                  90

<210> SEQ ID NO 6
<211> LENGTH: 2246
<212> TYPE: DNA
<213> ORGANISM: Mus sp.
<220> FEATURE:
<221> NAME/KEY: CDS
<222> LOCATION: (364)..(1887)

<400> SEQUENCE: 6
tgggtctttg gggaggcagg ttcccaagtg agtttattta ccttgagttg atcgatattt      60
gttacatgtc ctcctaggaa cagggattat tatttctgta aaagaaaag atagagcagg      120 ccatggcggc ccaacaggta aagcagctcg ccaccaaacc accaaacctg atgtcctgac      180
tttgatcctt gctgtctaca tggtgaaaga gagagctgag tcctgcaggc tcttctctga      240
ctgtcacgaa tgtgccatgg catacacaca cagaaaagag agagagagag agagagacag      300
acagacagac actgactgac tgactgccct ttttgtctca gcaggcggag cagagtatcc      360 agc atg ctg tcc cga cgc ctt ggt aag cgc tcc ctc ttg gga gcc cgg      408
    Met Leu Ser Arg Arg Leu Gly Lys Arg Ser Leu Leu Gly Ala Arg
      1               5                  10                  15 gtg ttg gga cct agt gcc gct gaa gta cca tca ggg gcc acc ctg cct      456
Val Leu Gly Pro Ser Ala Ala Glu Val Pro Ser Gly Ala Thr Leu Pro
                 20                  25                  30 ctg gag cca cag ata gaa gtg ccg gaa gga gcc atg tcc ctg tcc cca      504
Leu Glu Pro Gln Ile Glu Val Pro Glu Gly Ala Met Ser Leu Ser Pro
             35                  40                  45 ctc acc tct aag gac cct gtg tgc cag gag cag ccc aag gag ctc ctc      552
Leu Thr Ser Lys Asp Pro Val Cys Gln Glu Gln Pro Lys Glu Leu Leu
         50                  55                  60 aaa gct ctg gga acc tca ggc cac cca cag gtg gcc ttt cag cct gga      600
Lys Ala Leu Gly Thr Ser Gly His Pro Gln Val Ala Phe Gln Pro Gly
 65                  70                  75
```

-continued

| | |
|---|---|
| cag aag gtc tgt gtg tgg tat gga ggt cag gag tgc aag ggc ctg gtg<br>Gln Lys Val Cys Val Trp Tyr Gly Gly Gln Glu Cys Lys Gly Leu Val<br>80                         85                         90                         95 | 648 |
| gag cag cac agc tgg gcc gag gac aag gtg acc gtc cgg ctg ctg gac<br>Glu Gln His Ser Trp Ala Glu Asp Lys Val Thr Val Arg Leu Leu Asp<br>                          100                        105                      110 | 696 |
| cag aag tta cag att cgc tgt aaa gtg gaa gag gtg tgg ctg gcg gag<br>Gln Lys Leu Gln Ile Arg Cys Lys Val Glu Glu Val Trp Leu Ala Glu<br>               115                        120                      125 | 744 |
| ctg cag ggt agc gca tcc cac gtg cca gcc ttg gag ccc gga gcc cag<br>Leu Gln Gly Ser Ala Ser His Val Pro Ala Leu Glu Pro Gly Ala Gln<br>         130                        135                      140 | 792 |
| gtg cca gcc tac aga ccg gtg tct agg aac atc gac gtc ccg aag agg<br>Val Pro Ala Tyr Arg Pro Val Ser Arg Asn Ile Asp Val Pro Lys Arg<br>145                         150                        155 | 840 |
| aag tcg gat gcg gtg gag atg gac gag atg atg gcc gcc atg gtg ctg<br>Lys Ser Asp Ala Val Glu Met Asp Glu Met Met Ala Ala Met Val Leu<br>160                         165                        170                      175 | 888 |
| acg tct ctg tct tgc agt ccc gtt gtg cag agt cct cct ggg gct gag<br>Thr Ser Leu Ser Cys Ser Pro Val Val Gln Ser Pro Pro Gly Ala Glu<br>                          180                        185                      190 | 936 |
| ccc atc ttc tct gtt tcc cgt gca gcc tgc ggt gac ccg tgg aag gag<br>Pro Ile Phe Ser Val Ser Arg Ala Ala Cys Gly Asp Pro Trp Lys Glu<br>         195                        200                      205 | 984 |
| agc ggt gat gtt tca gac agc ggc agc agc ggg cac tgg agc ggg agc<br>Ser Gly Asp Val Ser Asp Ser Gly Ser Ser Gly His Trp Ser Gly Ser<br>         210                        215                      220 | 1032 |
| agt ggc agc tct acc ccc tcg ccg ccc cat ccg cag gcc agc ccc aag<br>Ser Gly Ser Ser Thr Pro Ser Pro Pro His Pro Gln Ala Ser Pro Lys<br>225                         230                        235 | 1080 |
| tac ctg ggg gat gcc ttt ggg tct ccc caa act gat cat ggc ttt gag<br>Tyr Leu Gly Asp Ala Phe Gly Ser Pro Gln Thr Asp His Gly Phe Glu<br>240                         245                        250                      255 | 1128 |
| act gat cct gac cct ttc ctg tta gac gaa cca gcc cca cga aag agg<br>Thr Asp Pro Asp Pro Phe Leu Leu Asp Glu Pro Ala Pro Arg Lys Arg<br>                          260                        265                      270 | 1176 |
| agg aac tcc gtg aag gtg atg tac aag tgc ctg tgg ccc agc tgt ggc<br>Arg Asn Ser Val Lys Val Met Tyr Lys Cys Leu Trp Pro Ser Cys Gly<br>         275                        280                      285 | 1224 |
| aaa gtt ctc cgt tca att gtg ggc atc aaa cga cac gtc aaa gcc ctc<br>Lys Val Leu Arg Ser Ile Val Gly Ile Lys Arg His Val Lys Ala Leu<br>         290                        295                      300 | 1272 |
| cac ctg ggg gac act gtt gac tct gat cag ttc aag cgg gag gaa gac<br>His Leu Gly Asp Thr Val Asp Ser Asp Gln Phe Lys Arg Glu Glu Asp<br>305                         310                        315 | 1320 |
| ttt tac tac aca gag atg cag atg aaa gag gaa tct gct cag gct gtg<br>Phe Tyr Tyr Thr Glu Met Gln Met Lys Glu Glu Ser Ala Gln Ala Val<br>320                         325                        330                      335 | 1368 |
| gct gct ccc cct gcc cct ggg aca cct atg ggc gag cca gcg tcc acc<br>Ala Ala Pro Pro Ala Pro Gly Thr Pro Met Gly Glu Pro Ala Ser Thr<br>                          340                        345                      350 | 1416 |
| tcc agg gtg acc agc ccg tcc ctt gct gct ctt tca ttg cct cca gcc<br>Ser Arg Val Thr Ser Pro Ser Leu Ala Ala Leu Ser Leu Pro Pro Ala<br>         355                        360                      365 | 1464 |
| aag gtc cag tca tct ggc cca gaa cac cct ggc ctg gag tct tct ctg<br>Lys Val Gln Ser Ser Gly Pro Glu His Pro Gly Leu Glu Ser Ser Leu<br>         370                        375                      380 | 1512 |
| ccc tca gtt gca ctc agc aag tca gct cct ggc tct ttc tgg cac att<br>Pro Ser Val Ala Leu Ser Lys Ser Ala Pro Gly Ser Phe Trp His Ile<br>385                         390                        395 | 1560 |

```
cag gct gac cat gca tat cag gct ctg cca tcc ttc cag atc cct gtt    1608
Gln Ala Asp His Ala Tyr Gln Ala Leu Pro Ser Phe Gln Ile Pro Val
400                 405                 410                 415 tcc ccc cac atc tat acc agc atc agc tgg gct gct gcc cct acc acc    1656
Ser Pro His Ile Tyr Thr Ser Ile Ser Trp Ala Ala Ala Pro Thr Thr
                420                 425                 430 acc tcc tcc ctc tct ccg gtc cga agc cgc tct ctc agc ttc agc gag    1704
Thr Ser Ser Leu Ser Pro Val Arg Ser Arg Ser Leu Ser Phe Ser Glu
            435                 440                 445 ccc cag cag ccg cca cct aca gtg aag tct cac ctg att gtc acc tcc    1752
Pro Gln Gln Pro Pro Pro Thr Val Lys Ser His Leu Ile Val Thr Ser
        450                 455                 460 cca ccc cgt gct cag agc agc acc agg aaa gcc cgt gga gag gcc aag    1800
Pro Pro Arg Ala Gln Ser Ser Thr Arg Lys Ala Arg Gly Glu Ala Lys
465                 470                 475 aag tgc cgt aag gtg tac ggc atc gag cac cgg gac cag tgg tgc aca    1848
Lys Cys Arg Lys Val Tyr Gly Ile Glu His Arg Asp Gln Trp Cys Thr
480                 485                 490                 495 gcc tgc cgg tgg aag aag gcc tgc cag cgc ttc ctg gac tgagcctgcc    1897
Ala Cys Arg Trp Lys Lys Ala Cys Gln Arg Phe Leu Asp
                500                 505 tcactagccc cgcttctcac cctgcctggc agccgggaag cctccaggcc tgcagccatc    1957
agcagaacac agggagatga tgtggcgtgg atgtgggcag ctgggctcc attggctaag     2017 atagaacact taaaaacact tttctccccc ttgttgggag tgctttattt tttaaaagca    2077
aacctaaatg aaactatttt tcccttaaa ataggagaga gccaaaattg accaagggta    2137
ttctgcagcg aaccggagac caaagagtta ccctacccc taccccattc caccctctct    2197
gggactacat atgcatcaag agtaggacag gatgctgcct tgcctggtt              2246

<210> SEQ ID NO 7
<211> LENGTH: 508
<212> TYPE: PRT
<213> ORGANISM: Mus sp.

<400> SEQUENCE: 7

Met Leu Ser Arg Arg Leu Gly Lys Arg Ser Leu Leu Gly Ala Arg Val
1               5                   10                  15

Leu Gly Pro Ser Ala Ala Glu Val Pro Ser Gly Ala Thr Leu Pro Leu
            20                  25                  30

Glu Pro Gln Ile Glu Val Pro Glu Gly Ala Met Ser Leu Ser Pro Leu
        35                  40                  45

Thr Ser Lys Asp Pro Val Cys Gln Glu Gln Pro Lys Glu Leu Leu Lys
    50                  55                  60

Ala Leu Gly Thr Ser Gly His Pro Gln Val Ala Phe Gln Pro Gly Gln
65                  70                  75                  80

Lys Val Cys Val Trp Tyr Gly Gly Gln Glu Cys Lys Gly Leu Val Glu
                85                  90                  95

Gln His Ser Trp Ala Glu Asp Lys Val Thr Val Arg Leu Leu Asp Gln
            100                 105                 110

Lys Leu Gln Ile Arg Cys Lys Val Glu Glu Val Trp Leu Ala Glu Leu
        115                 120                 125

Gln Gly Ser Ala Ser His Val Pro Ala Leu Glu Pro Gly Ala Gln Val
    130                 135                 140

Pro Ala Tyr Arg Pro Val Ser Arg Asn Ile Asp Val Pro Lys Arg Lys
145                 150                 155                 160
```

-continued

```
Ser Asp Ala Val Glu Met Asp Glu Met Met Ala Ala Met Val Leu Thr
                165                 170                 175
Ser Leu Ser Cys Ser Pro Val Val Gln Ser Pro Gly Ala Glu Pro
            180                 185                 190
Ile Phe Ser Val Ser Arg Ala Ala Cys Gly Asp Pro Trp Lys Glu Ser
        195                 200                 205
Gly Asp Val Ser Asp Ser Gly Ser Ser Gly His Trp Ser Gly Ser Ser
    210                 215                 220
Gly Ser Ser Thr Pro Ser Pro Pro His Pro Gln Ala Ser Pro Lys Tyr
225                 230                 235                 240
Leu Gly Asp Ala Phe Gly Ser Pro Gln Thr Asp His Gly Phe Glu Thr
                245                 250                 255
Asp Pro Asp Pro Phe Leu Leu Asp Glu Pro Ala Pro Arg Lys Arg Arg
            260                 265                 270
Asn Ser Val Lys Val Met Tyr Lys Cys Leu Trp Pro Ser Cys Gly Lys
        275                 280                 285
Val Leu Arg Ser Ile Val Gly Ile Lys Arg His Val Lys Ala Leu His
    290                 295                 300
Leu Gly Asp Thr Val Asp Ser Asp Gln Phe Lys Arg Glu Glu Asp Phe
305                 310                 315                 320
Tyr Tyr Thr Glu Met Gln Met Lys Glu Glu Ser Ala Gln Ala Val Ala
                325                 330                 335
Ala Pro Pro Ala Pro Gly Thr Pro Met Gly Glu Pro Ala Ser Thr Ser
            340                 345                 350
Arg Val Thr Ser Pro Ser Leu Ala Ala Leu Ser Leu Pro Pro Ala Lys
        355                 360                 365
Val Gln Ser Ser Gly Pro Glu His Pro Gly Leu Glu Ser Ser Leu Pro
    370                 375                 380
Ser Val Ala Leu Ser Lys Ser Ala Pro Gly Ser Phe Trp His Ile Gln
385                 390                 395                 400
Ala Asp His Ala Tyr Gln Ala Leu Pro Ser Phe Gln Ile Pro Val Ser
                405                 410                 415
Pro His Ile Tyr Thr Ser Ile Ser Trp Ala Ala Ala Pro Thr Thr Thr
            420                 425                 430
Ser Ser Leu Ser Pro Val Arg Ser Arg Ser Leu Ser Phe Ser Glu Pro
        435                 440                 445
Gln Gln Pro Pro Pro Thr Val Lys Ser His Leu Ile Val Thr Ser Pro
    450                 455                 460
Pro Arg Ala Gln Ser Ser Thr Arg Lys Ala Arg Gly Glu Ala Lys Lys
465                 470                 475                 480
Cys Arg Lys Val Tyr Gly Ile Glu His Arg Asp Gln Trp Cys Thr Ala
                485                 490                 495
Cys Arg Trp Lys Lys Ala Cys Gln Arg Phe Leu Asp
            500                 505
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agacgaacca gccccacgaa agag                                           24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggctgct ggggctcgct gaag                                              24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgggtctttg gggaggcagg ttc                                               23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaccaggcaa ggcagcatcc                                                   20

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctaaaatcct tgaactctgt ggcgacctg                                         29

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgcgtcgtc tgaacattgg gtctgg                                            26

<210> SEQ ID NO 14
<211> LENGTH: 163
<212> TYPE: DNA
<213> ORGANISM: Homo sapiens
<220> FEATURE:
<223> OTHER INFORMATION: Chondromodulin-I gene promoter

<400> SEQUENCE: 14
aggtgaggcg ctggaagggg tggggaccgc tgggctggcc caggcgggac cgtgcaccgt        60
gtgtgcgcgc ggcgttgaaa tgccctgcac gtcggggcag cgggacagat cccagggtgc       120

```
ccagggagtc tccaagtgcc tcactcctcc cgccgcaaac atg                    163
```

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gagtggggag tcggcggga aacag                                         25
```

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cagtcgggcg tggaagtggg atgagc                                       26
```

<210> SEQ ID NO 17
<211> LENGTH: 20
<212> TYPE: DNA
<213> ORGANISM: Homo sapiens
<220> FEATURE:
<223> OTHER INFORMATION: Chondromodulin-I gene cis-element

<400> SEQUENCE: 17

```
gctggaaggg gtggggaccg                                              20
```

<210> SEQ ID NO 18
<211> LENGTH: 270
<212> TYPE: DNA
<213> ORGANISM: Homo sapiens

<400> SEQUENCE: 18

```
atctacacca gtgtcagctg ggctgctgcc cctccgccg cctgctctct ctctccggtc   60
cggagccggt cgctaagctt cagcgagccc cagcagccag cacctgcgat gaaatctcat  120
ctgatcgtca cttctccacc ccgggcccag agtggtgcca ggaaagcccg aggggaggct  180
aagaagtgcc gcaaggtgta tggcatcgag caccgggacc agtggtgcac ggcctgccgg  240
tggaagaagg cctgccagcg ctttctggac                                   270
```

<210> SEQ ID NO 19
<211> LENGTH: 90
<212> TYPE: PRT
<213> ORGANISM: Mus sp.

<400> SEQUENCE: 19

Ile Tyr Thr Ser Ile Ser Trp Ala Ala Ala Pro Thr Thr Thr Ser Ser
  1               5                  10                  15

Leu Ser Pro Val Arg Ser Arg Ser Leu Ser Phe Ser Glu Pro Gln Gln
             20                  25                  30

Pro Pro Pro Thr Val Lys Ser His Leu Ile Val Thr Ser Pro Pro Arg
         35                  40                  45

Ala Gln Ser Ser Thr Arg Lys Ala Arg Gly Glu Ala Lys Lys Cys Arg
     50                  55                  60

Lys Val Tyr Gly Ile Glu His Arg Asp Gln Trp Cys Thr Ala Cys Arg

| 65 | | | 70 | | | 75 | | | 80 | |
|---|---|---|---|---|---|---|---|---|---|---|

Trp Lys Lys Ala Cys Gln Arg Phe Leu Asp
                  85                  90

<210> SEQ ID NO 20
<211> LENGTH: 270
<212> TYPE: DNA
<213> ORGANISM: Mus sp.

<400> SEQUENCE: 20

```
atctatacca gcatcagctg ggctgctgcc cctaccacca cctcctccct ctctccggtc      60
cgaagccgct ctctcagctt cagcgagccc agcagccgc cacctacagt gaagtctcac     120
ctgattgtca cctccccacc ccgtgctcag agcagcacca ggaaagcccg tggagaggcc    180
aagaagtgcc gtaaggtgta cggcatcgag caccgggacc agtggtgcac agcctgccgg    240
tggaagaagg cctgccagcg cttcctggac                                     270
```

<210> SEQ ID NO 21
<211> LENGTH: 20
<212> TYPE: DNA
<213> ORGANISM: Homo sapiens
<220> FEATURE:
<223> OTHER INFORMATION: Chondromodulin-I gene cis-element

<400> SEQUENCE: 21

```
gctagaaggg gtggggaccg                                                 20
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding mouse Col2a1

<400> SEQUENCE: 22

```
gctcatcgcc gcggtcctac g                                               21
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding mouse Col2a1

<400> SEQUENCE: 23

```
ctcgccaggt tcgccaggat tg                                              22
```

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding human COL2A1

<400> SEQUENCE: 24

```
ccccggcact cctggcactg at                                              22
```

<210> SEQ ID NO 25

-continued

```
<211> LENGTH: 24
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding human COL2A1

<400> SEQUENCE: 25
cttgggcacc tcgggctcct ttag                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding rabbit Col2a1

<400> SEQUENCE: 26
gccacgctca agtccctcaa caac                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
      Synthetically designed oligonucleotide primer to amplify DNA
      encoding rabbit Col2a1

<400> SEQUENCE: 27
acagcaggcg caggaaggtc atct                                              24

<210> SEQ ID NO 28
<211> LENGTH: 163
<212> TYPE: DNA
<213> ORGANISM: Homo sapiens

<400> SEQUENCE: 28
aggtgaggcg ctagaagggg tggggaccgc tgggctggcc caggcgggac cgtgcaccgt        60
gtgtgcgcgc ggcgttgaaa tgccctgcac gtcggggcag cgggacagat cccagggtgc       120
ccagggagtc tccaagtgcc tcactcctcc cgccgcaaac atg                         163

<210> SEQ ID NO 29
<211> LENGTH: 60
<212> TYPE: DNA
<213> ORGANISM: Homo sapiens

<400> SEQUENCE: 29
gctggaaggg gtggggaccg gctggaaggg gtggggaccg gctggaaggg gtggggaccg        60
```